United States Patent [19]
Warren et al.

[11] Patent Number: 5,665,781
[45] Date of Patent: Sep. 9, 1997

[54] USE OF UNSATURATED ALDEHYDE AND ALKANOL DERIVATIVES FOR THEIR MOSQUITO REPELLENCY PROPERTIES

[75] Inventors: Craig B. Warren, Monmouth Beach; Anna B. Marin, Long Branch, both of N.J.; Jerry F. Butler, Gainesville, Fla.

[73] Assignees: International Flavors & Fragrances Inc., New York, N.Y.; The University of Florida, Gainesville, Fla.

[21] Appl. No.: 733,386

[22] Filed: Oct. 18, 1996

Related U.S. Application Data

[63] Continuation-in-part of Ser. No. 496,124, Jun. 27, 1995, Pat. No. 5,576,010, which is a continuation-in-part of Ser. No. 253,244, Jun. 2, 1994, Pat. No. 5,472,701, which is a division of Ser. No. 61,044, May 14, 1993, Pat. No. 5,464,626.

[51] Int. Cl.[6] ............................ A01N 35/02; A01N 25/08
[52] U.S. Cl. .......................... 514/703; 514/919; 424/409
[58] Field of Search ................................ 514/739, 919, 514/703, 698; 424/409

[56] References Cited

U.S. PATENT DOCUMENTS

| | | | |
|---|---|---|---|
| 2,564,664 | 8/1951 | Bartlett et al. | 514/703 |
| 2,947,780 | 8/1960 | Teegarden et al. | 260/488 |
| 4,049,828 | 9/1977 | Cole | 514/703 |
| 4,774,081 | 9/1988 | Flashinski et al. | 514/919 |
| 5,354,783 | 10/1994 | Marin et al. | 514/691 |
| 5,401,500 | 3/1995 | Warren et al. | 424/84 |

OTHER PUBLICATIONS

Kirk–Othmer Encyclopedia of Chemical Technology, 4th ed., John Wiley & Sons, New York, 1993, vol. 6, p. 209.
Wilson et al. (eds.), Comprehensive Analytical Chemistry, Elsevier Publishing Co., New York, 1968, p. 118.
Bender, Gary T., Principles of Chemical Instrumentation, W.B. Saunders Co., Philadelphia, 1987, p. 227.
Baugh, P.J. (ed.), Gas Chromatography A Practical Approach, Oxford University Press, New York, 1939, p. 50.
Arctander, *Perfume and Flavor Chemicals (Aroma Chemicals)*, vol. I, monograhs 649 and 650 (copy of front cover page and page containing monograph pages containing monographs 649 and 650), 1969.
King, *Chemicals Evaluated as insecticides and Repellents at Orlando, Fla*, Entomology Branch, Agricultural Research Service, U.S. Department of Agriculture, Agriculture Handbook No. 69, issued May 1954, pp. 179, 180, 120 and front cover page; of interest: Items 5366–5374, inclusive, and Item 3418.

*IFF Fragrance Ingredient Specifications Compendium*, published by International Flavors & Fragrances Inc., 1991, pp. 31, 32, 50 and front cover page; Items 155, 157, 158 and 244.

United States Patent Application Ser. No. 08/535,670, filed on Sep. 28, 1995, Marin et al.

Primary Examiner—John Pak
Attorney, Agent, or Firm—Arthur L. Liberman

[57] ABSTRACT

Described is a method of repelling *Aedes aegypti* for a finite period of time from a three-dimensional space inhabited by *Aedes aegypti* consisting essentially of the step of exposing a three-dimensional space to an effective Aedes aegypti-repelling concentration and quantity of an unsaturated aldehyde or alcohol derivative-containing composition of matter selected from the group consisting of:

(i) a mixture of compounds having the structures:

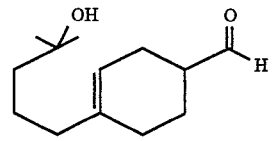

and

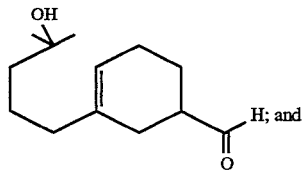

and (ii) a compound having the structure:

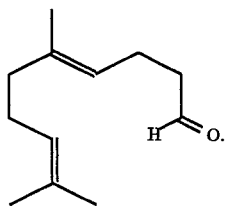

8 Claims, 16 Drawing Sheets

FIG.3-A
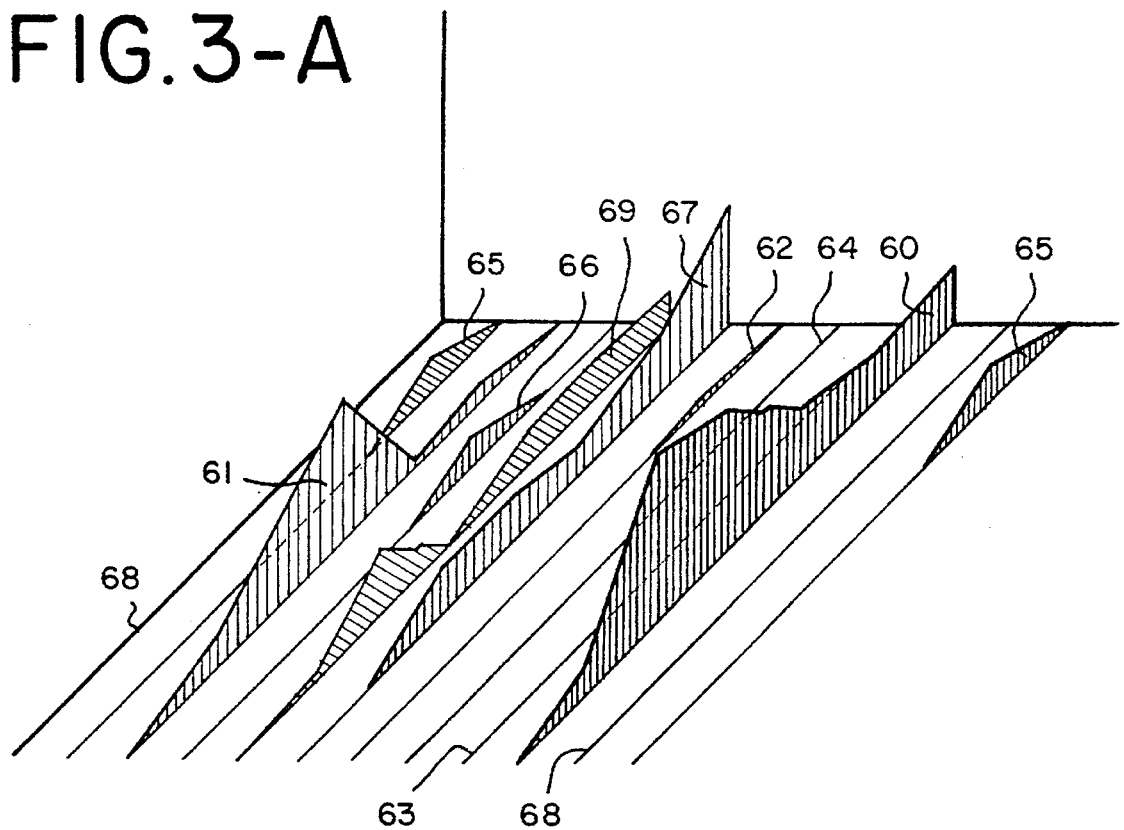
FIG.3-B
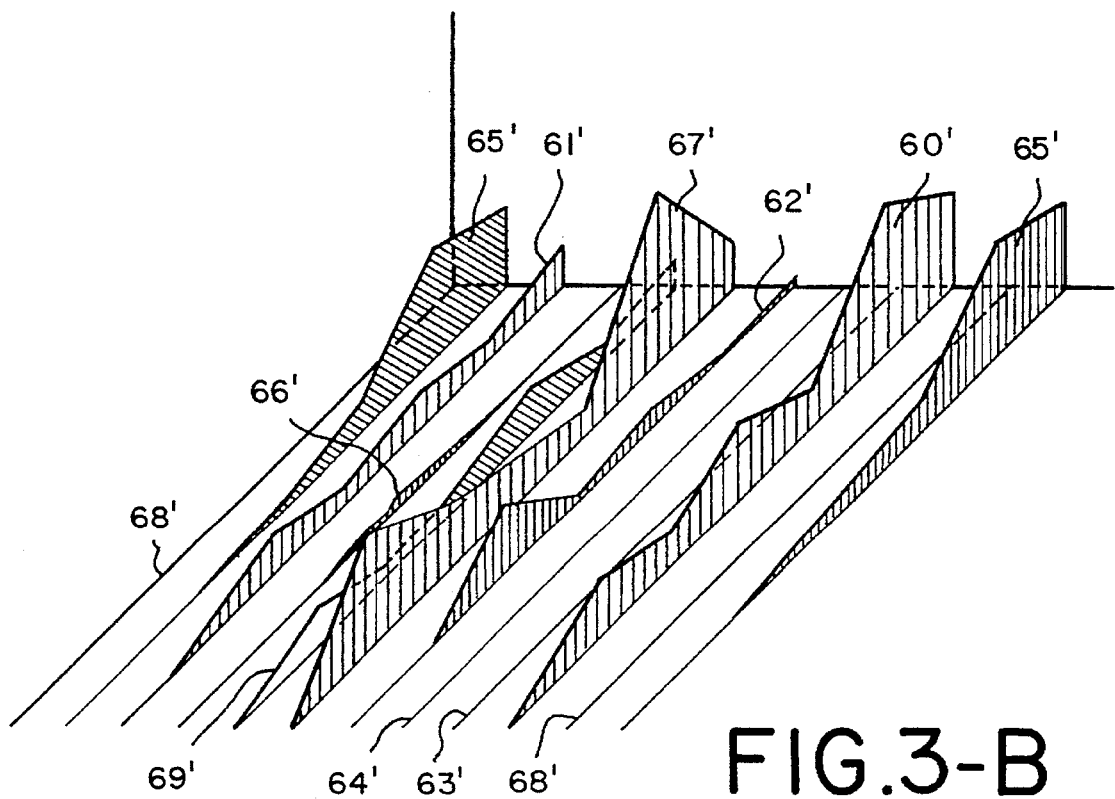

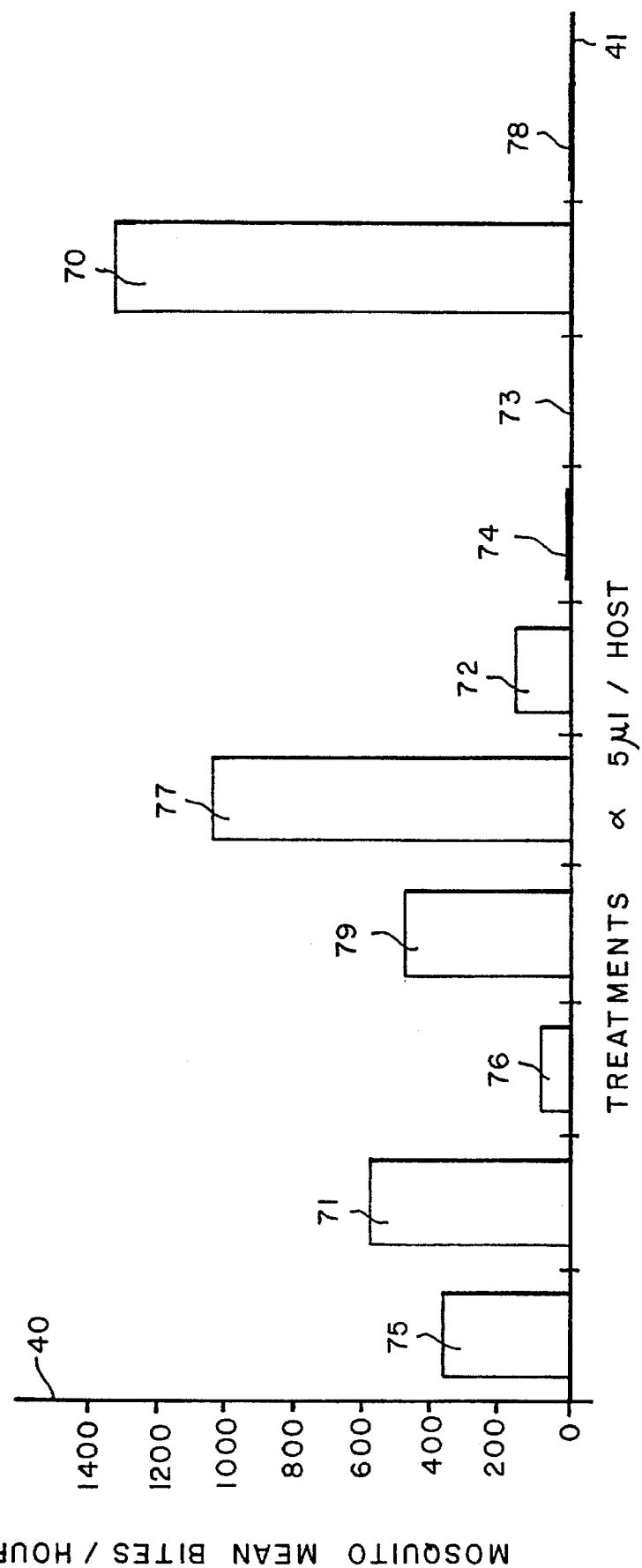

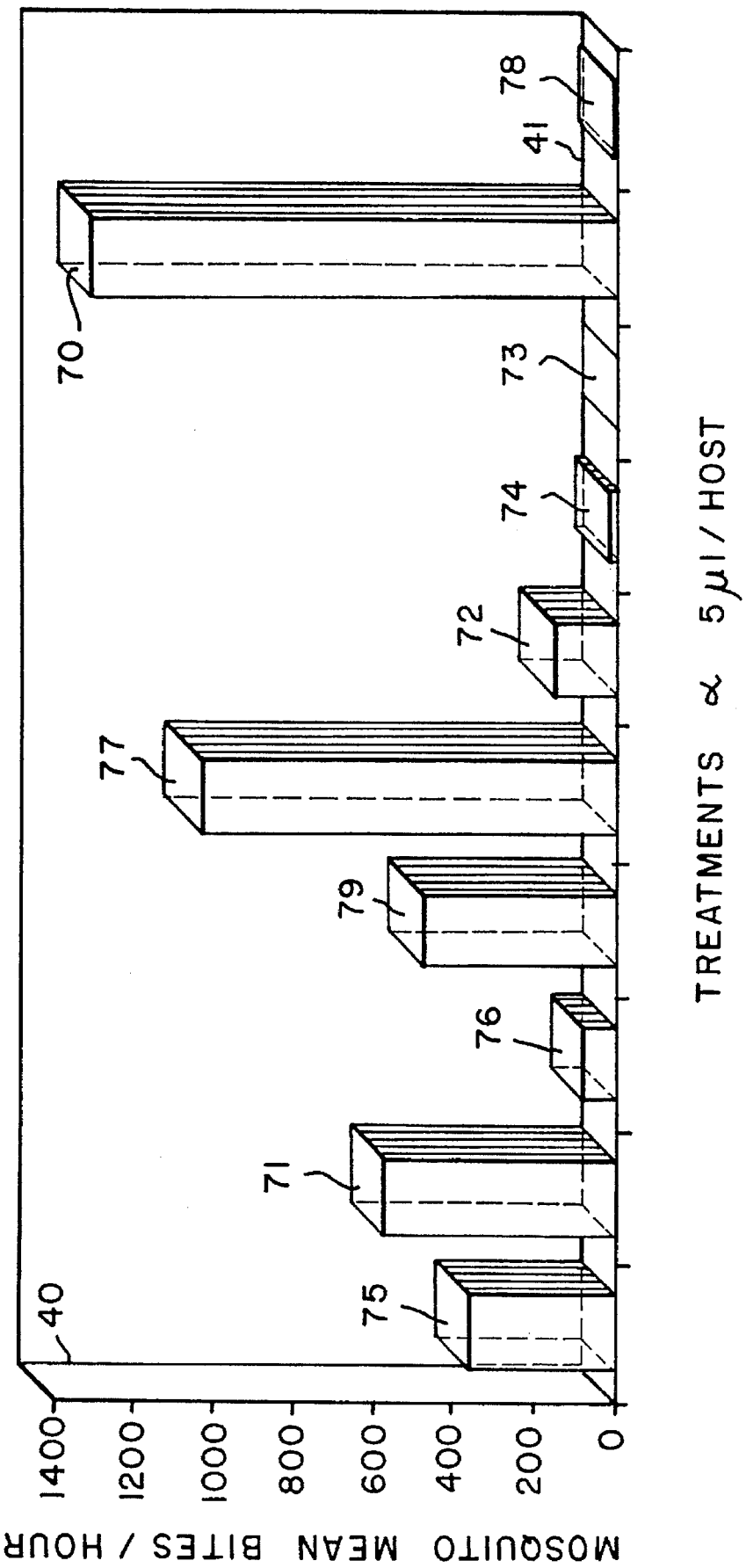

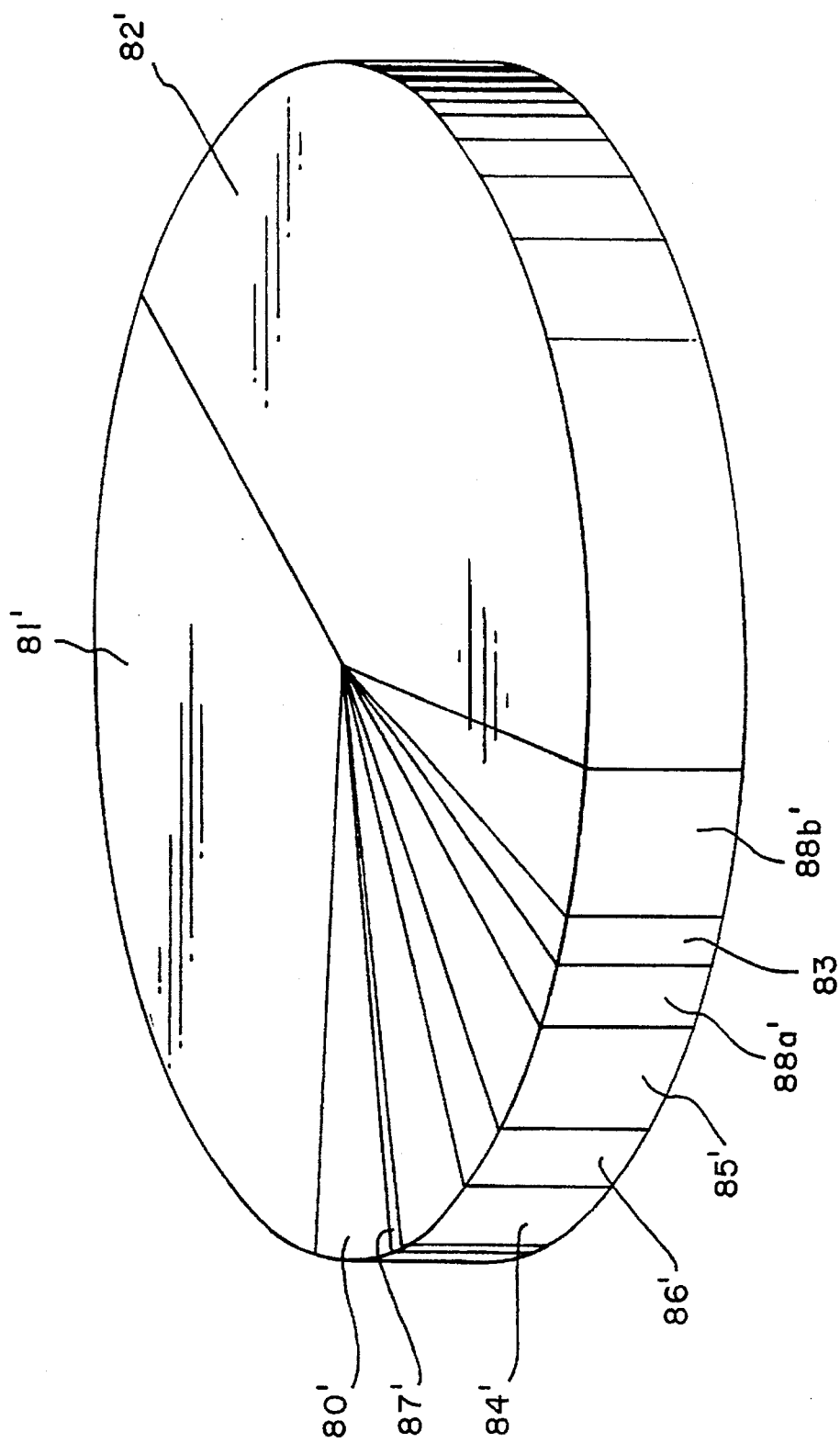

FIG. 7-A
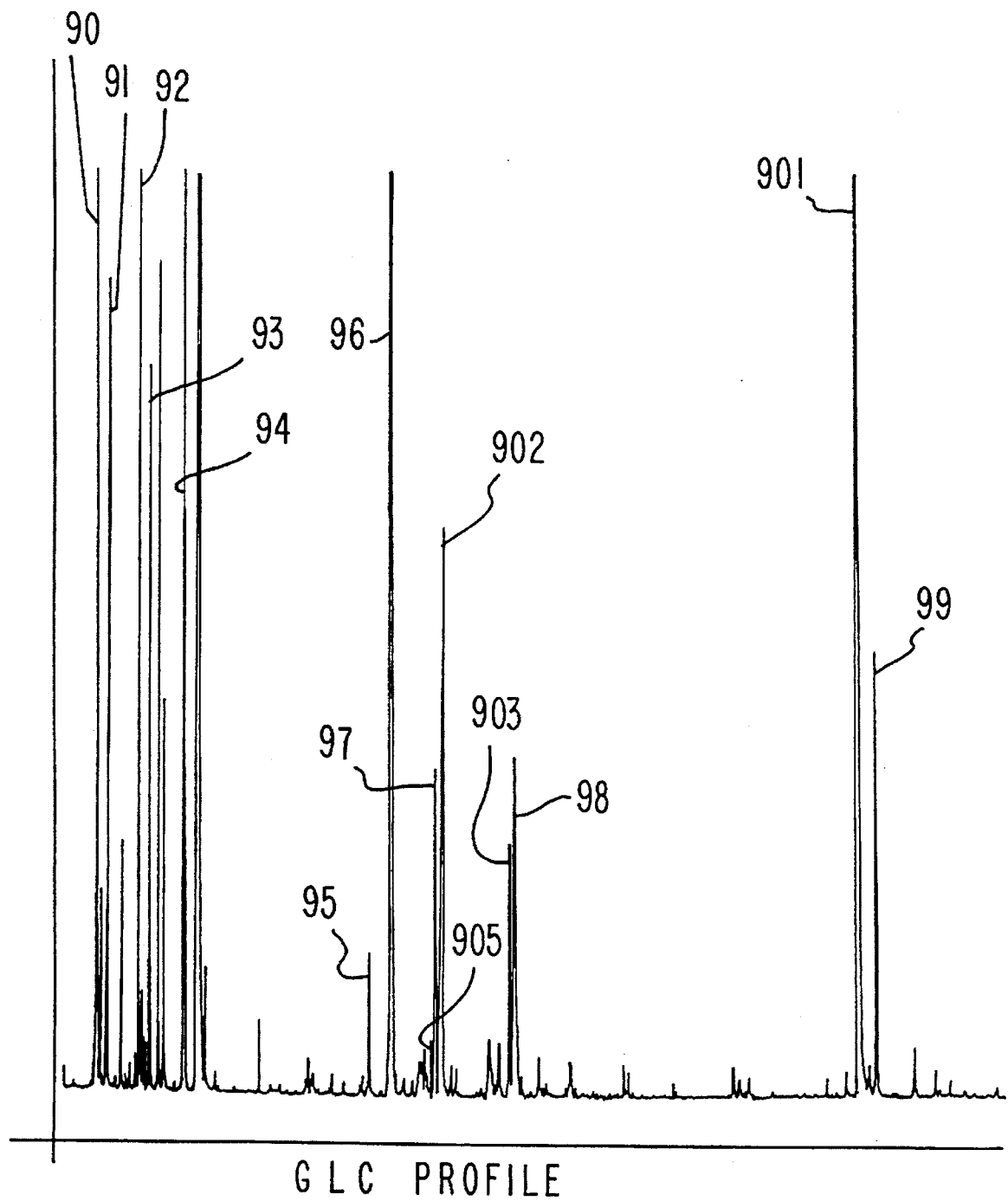
GLC PROFILE

FIG. 7-B
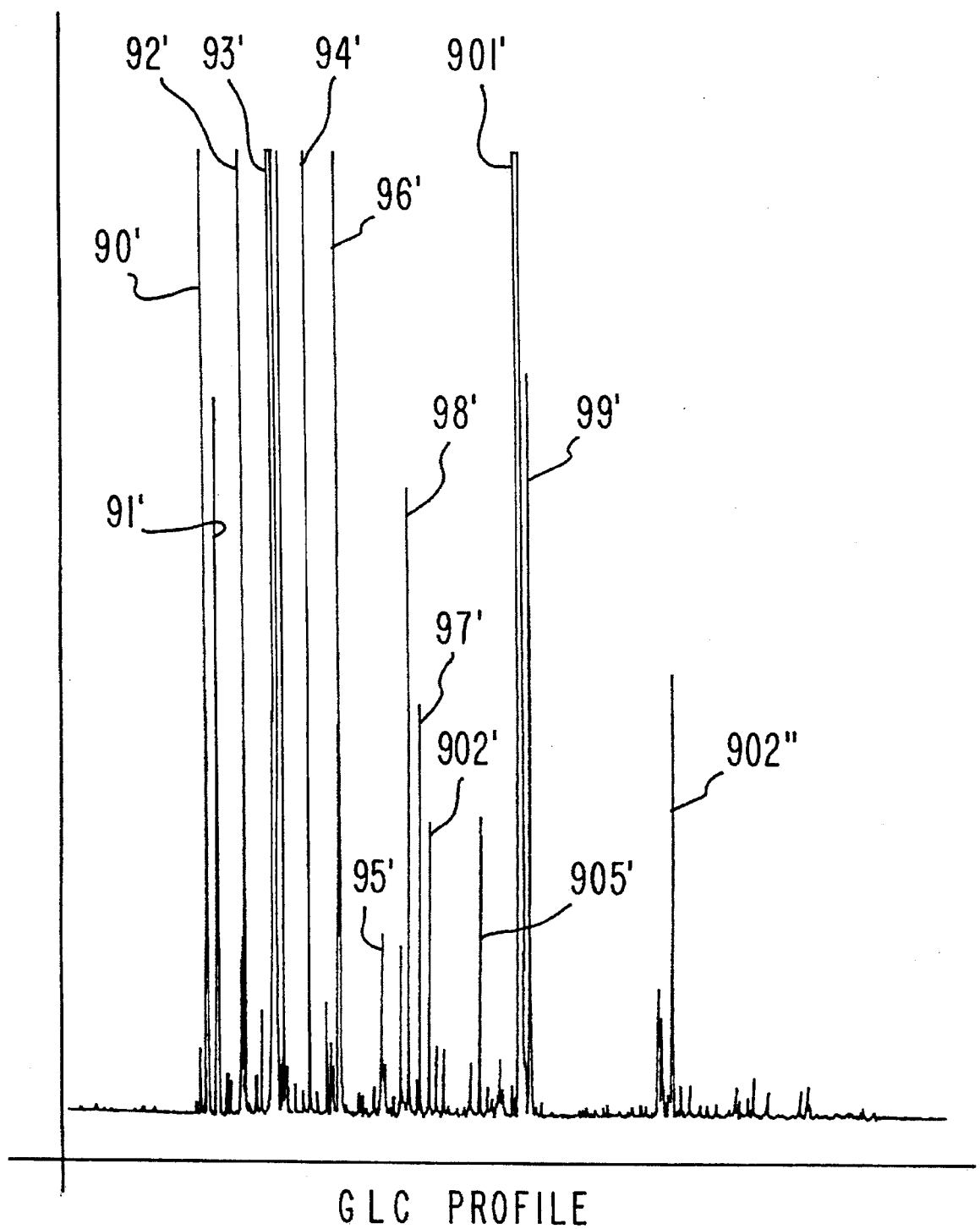
GLC PROFILE

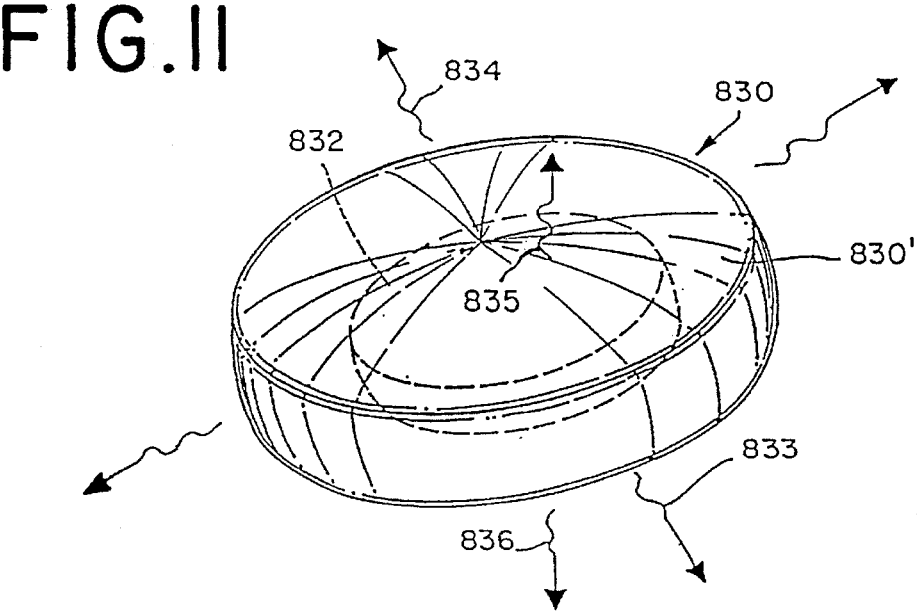
FIG.11
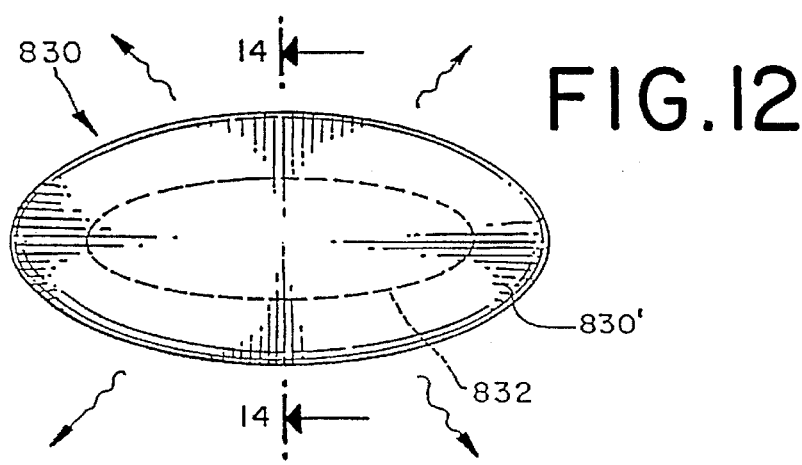
FIG.12
FIG.13
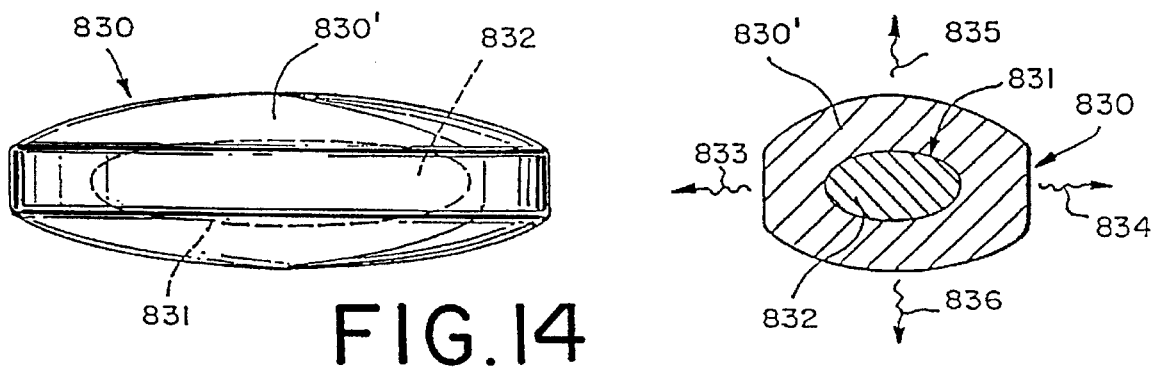
FIG.14

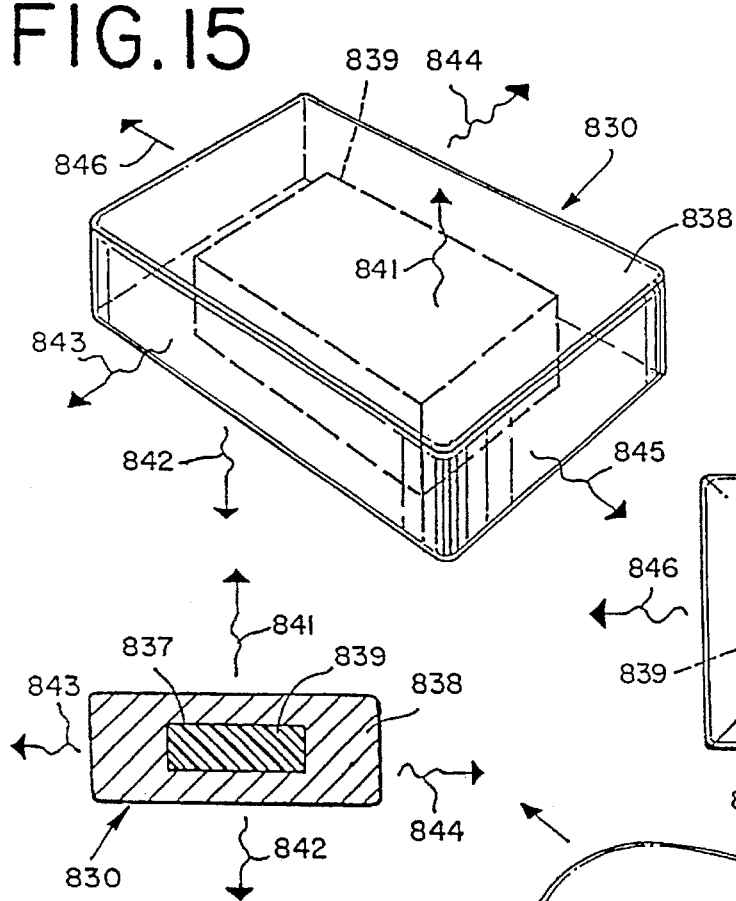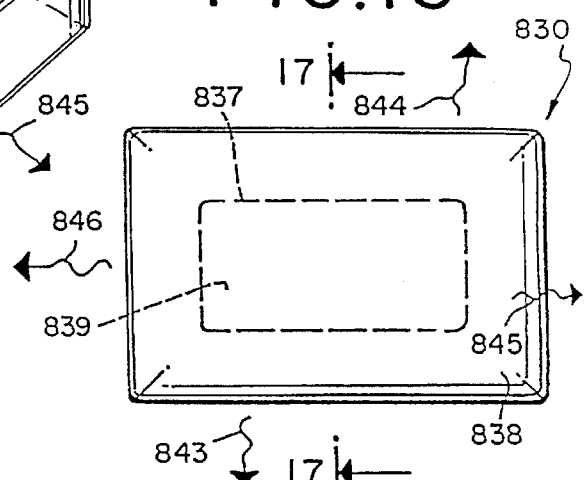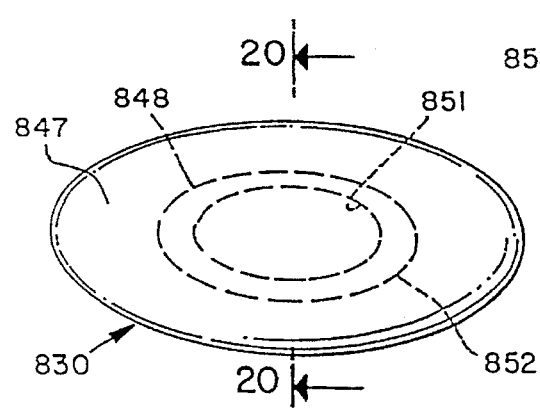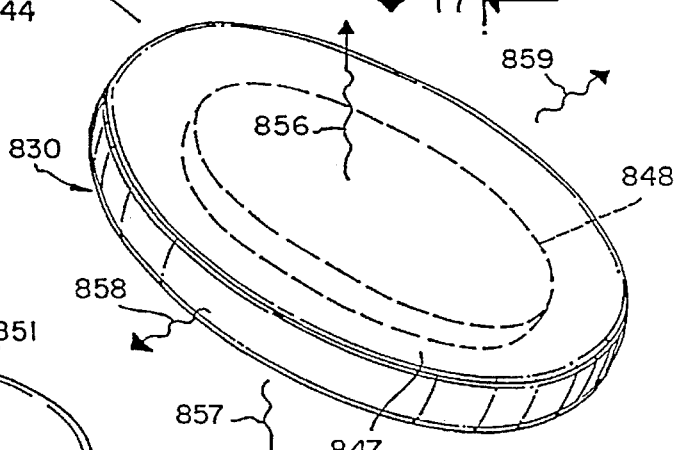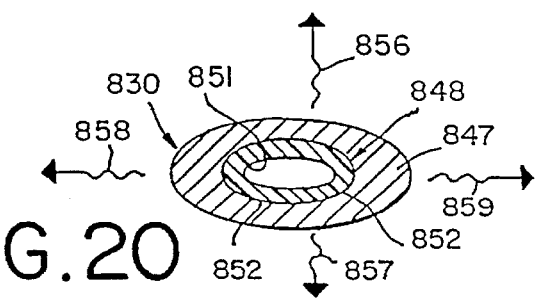

GLC PROFILE

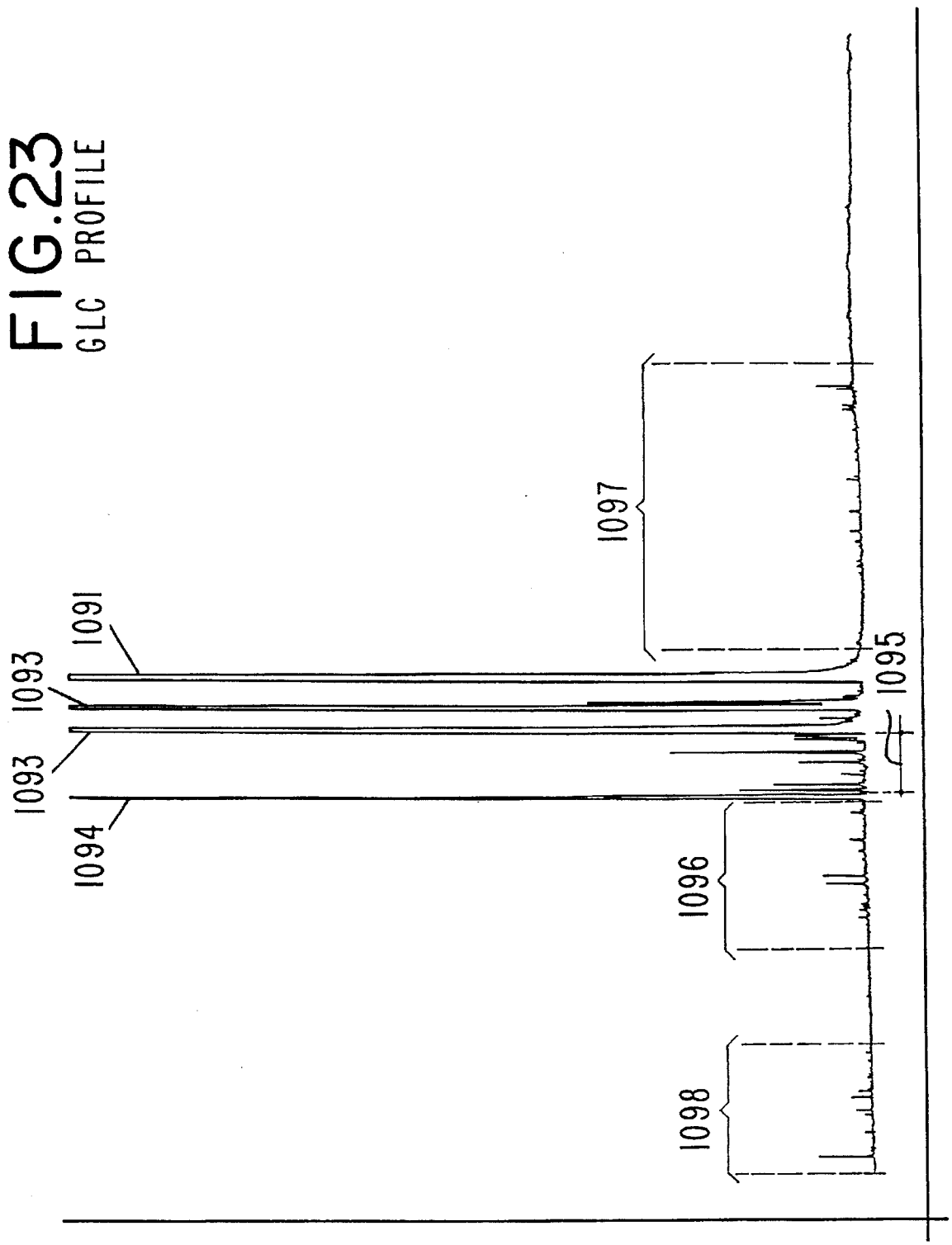

USE OF UNSATURATED ALDEHYDE AND ALKANOL DERIVATIVES FOR THEIR MOSQUITO REPELLENCY PROPERTIES

This Application is a Continuation-in-Part of Application for U.S. patent Ser. No. 08/496,124 filed on Jun. 27, 1995 (now U.S. Pat. No. 5,576,010), which, in turn, is a Continuation-in-Part of application for U.S. patent, Ser. No. 08/253,244 filed on Jun. 2, 1994 (now U.S. Pat. No. 5,472,701 issued on Dec. 5, 1995); which is a Divisional of Application for U.S. patent, Ser. No. 08/061,044 filed on May 14, 1993 (now U.S. Pat. No. 5,464,626 issued on Nov. 7, 1995).

Each of the foregoing applications discloses (but does not claim) the use as an insect repellent of GERALDEHYDE™ having the structure:

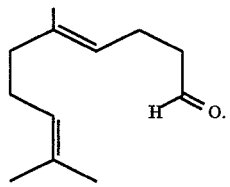

Co-pending Application for U.S. patent, Ser. No. 08/535,670 now abandoned (inventors: Anna Belle Marin and Jerry F. Butler, assigned jointly to the University of Florida and International Flavors & Fragrances Inc.) discloses and claims a method for repelling fire ants (*Solenopsis invicta* Buren) and horn flies (*Haematobia irritans* (Linnaeus)) using GERANIOL COEUR™ as defined according to the GLC profiles of FIGS. 22 and 23 described, infra.

BACKGROUND OF THE INVENTION

This invention relates to the use of unsaturated aldehyde or alcohol derivative-containing compositions of matter selected from the group consisting of:

(i) LYRAL®, a mixture of compounds having the structures:

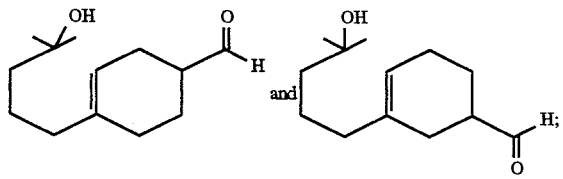

(ii) GERALDEHYDE™, having the structure:

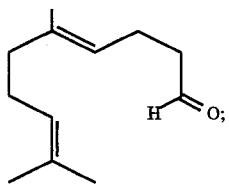

(iii) GERANIOL COEUR™ (both natural and synthetic), mixtures of compounds defined according to the GLC spectra of FIGS. 22 and 23 in repelling mosquitoes, *Aedes aegypti*.

This invention also relates to the use of such materials and compositions of matter in insect repellent soaps and the like wherein the compositions of matter are used as such or in combination in control release systems with polymers such as biodegradable polymers.

The prior art discloses a vast number of floral type fragrance materials useful in perfumery. However, such floral type materials in many instances are attractants rather than repellents for various insects including the wide variety of mosquitoes which proliferate in temperate, subtropical and tropical zones.

Thus, U.S. Pat. No. 2,947,780 issued on Aug. 2, 1960 discloses the perfumery use of the compound having the structure:

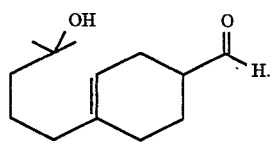

Arctander, "Perfume and Flavor Chemicals (*Aroma Chemicals*), Volume I, published in 1969 at monograph 649 discloses the perfume use of the mixture of compounds having the structures:

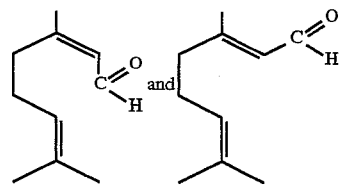

and at monograph 650 discloses the perfume use of the compound having the structure:

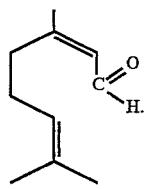

The international Flavors & Fragrances Inc. "FRAGRANCE INGREDIENT SPECIFICATIONS COMPENDIUM" published in 1990 discloses the perfumery use of GERALDEHYDE™ having the structure:

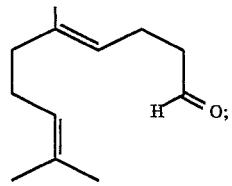

LYRAL®, a mixture of compounds having the structures:

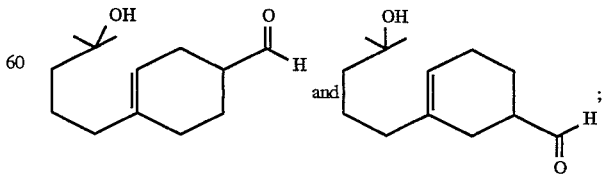

and GERANIOL COEUR™ defined according to the GLC spectra of FIGS. 22 and 23 described, infra.

However, none of the materials of the instant invention, that is, the compound having the structure:

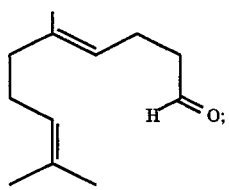

the mixture of compounds having the structures:

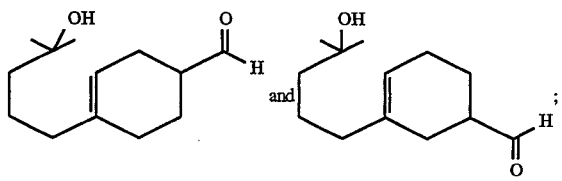

or the geraniol-containing composition defined according to the spectra of FIGS. 22 or 23 are not described for their use in repelling *Aedes aegypti* in any prior art.

Geraniol having the structure:

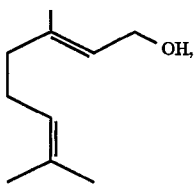

per se; as well as geraniol, first fraction of Java citronella oil; geraniol, second fraction of Java citronella oil; and, geraniol, last fraction of Java citronella oil; as well as geraniol, last fraction, high-boiling Java citronella oil are all indicated to have mosquito repelling properties (*Aedes aegypti* repelling properties) at Item Nos. 5366–5374, inclusive, on page 179 of King, "CHEMICALS EVALUATED AS INSECTICIDES AND REPELLENTS AT ORLANDO, Fla.", U.S. Department of Agriculture, Agriculture Handbook No. 69 issued May 1954.

Furthermore, CITRAL™, the mixture of compounds having the structures:

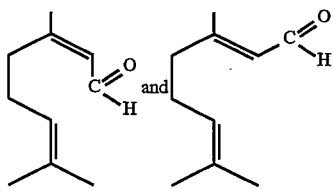

is indicated to have mosquito (*Aedes aegypti*) repellency properties at Item No. 3418 on page 120 of the King reference cited, supra.

Furthermore, U.S. Pat. No. 5,401,500 issued on Mar. 28, 1995 (effective date, Sep. 18, 1992) discloses that a mixture of 61.49% geraniol having the structure:

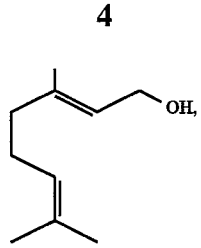

13.98 mole percent nerol and 24.53 mole percent citronellol have *Aedes aegypti*-repelling properties. PCT Application No. 91/15118 published on Oct. 17, 1991 (Beldock, et al) alleges the use of a mixture of geraniol in combination with terpineol, citronella and rhodenol extract as a repellent against ticks and biting flies, including mosquitoes and black flies. It is alleged in PCT Application No. 91/15118 that the composition of matter, TREO®, containing:

0.06% terpineol;

0.05% citronella;

0.08% rhodenol extract; and 0.06% geraniol is such a useful insect repellent composition.

However, nothing in the prior art published prior to the invention, defined in the instant case and defined by the claims of the instant case teaches applicant's invention.

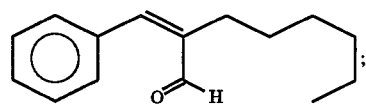

LYRAL®, a mixture of compounds having the structures:

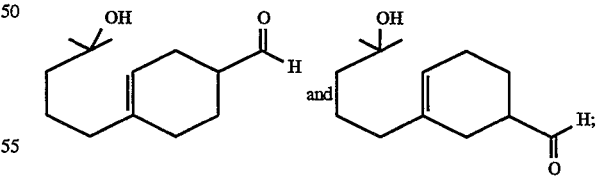

FLORALATE™, having the structure:

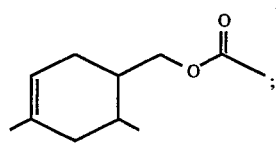

GERALDEHYDE™, having the structure:

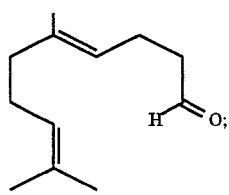

ISOPROXEN™, a mixture of compounds having the structures:

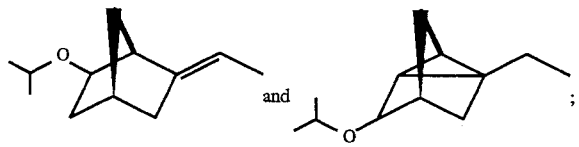

opoponax oil; cis-3-hexenyl acetate having the structure:

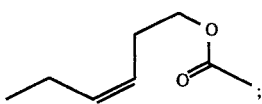

Figure 22:
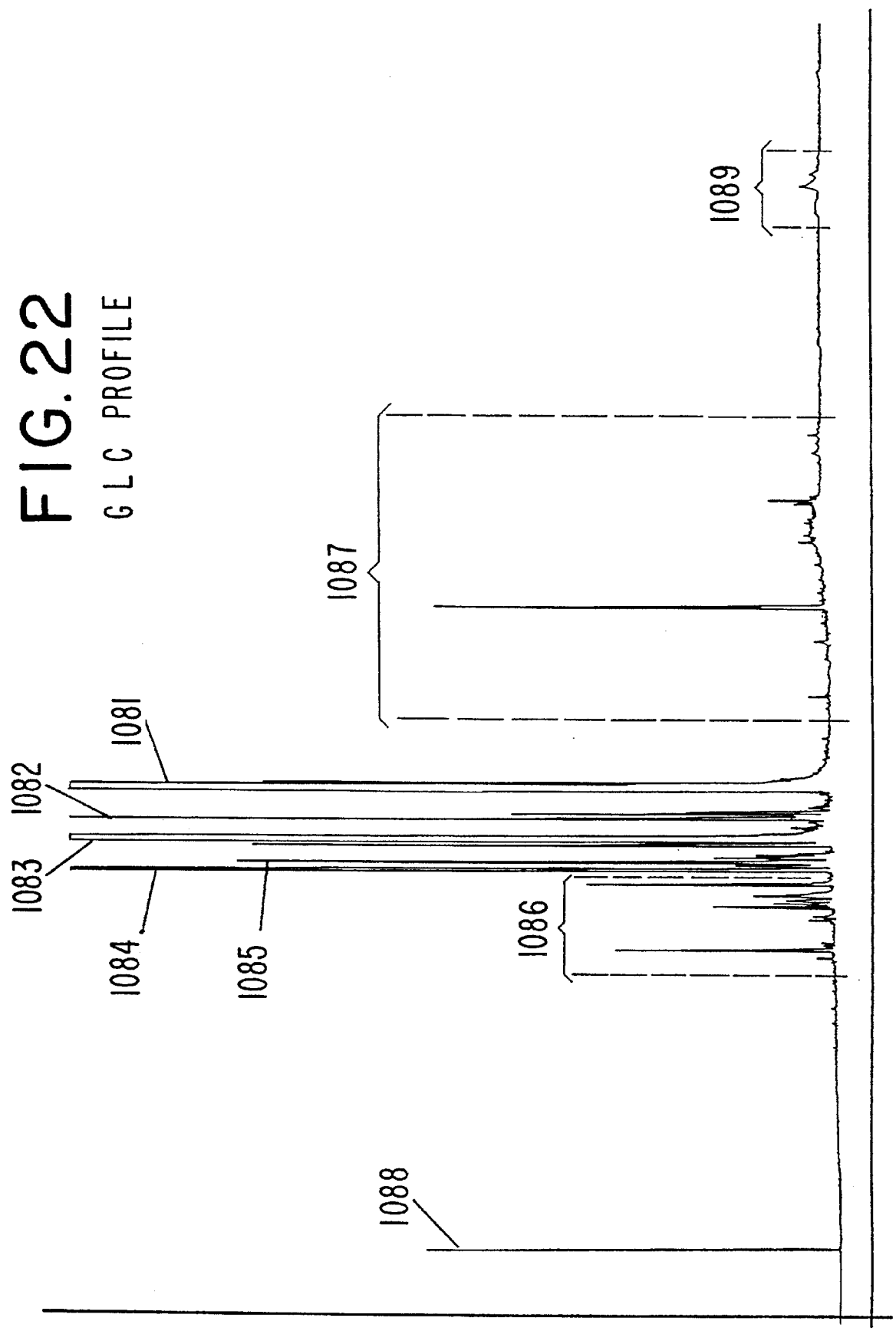

GERANIOL COEUR™, a geraniol-containing composition having the GLC spectra set forth in FIGS. 22 and 23 and produced by Examples I and II, infra; and MARANTHA™, having the structure:

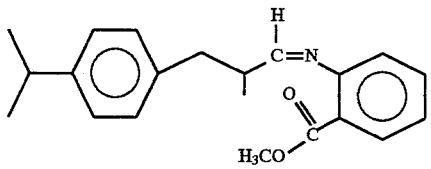

for a mean feeding contact time of one hour.

Figure 2:
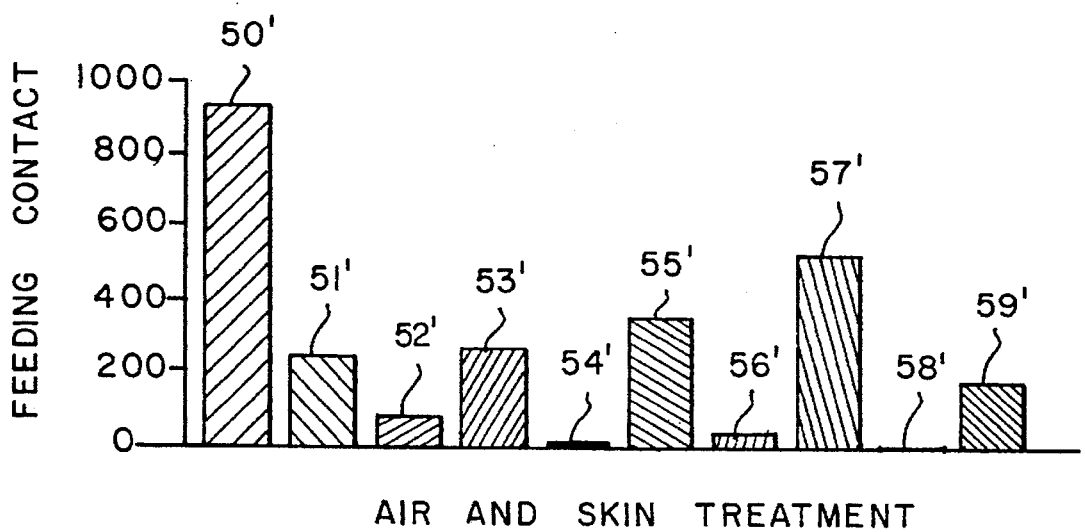

FIG. 2 is a bar graph showing the mean number of feeding contacts (on the "Y" axis) versus the particular treatment substance (on the "X" axis) for air, hexyl cinnamic aldehyde, FLORALATE™, GERALDEHYDE™, ISOPROXEN™, opoponax, cis-3-hexenyl acetate, GERANIOL COEUR™ and MARANTHA™ for a mean 2–6 hour feeding contact time.

FIG. 3A is a series of graphs depicted in three dimensions (in a rectangular mode for the "X" and "Y" axes) showing the relative attractiveness or repellency of air, GERANIOL COEUR™, ISOPROXEN™, hexyl cinnamic aldehyde, opoponax absolute (defined according to the GLC spectrum of FIG. 8, infra), MARANTHA™, cis3-hexenyl acetate, LYRAL®, GERALDEHYDE™, FLORALATE™ and air. The graphs are based on experiments run for a period of one hour with six intervals of ten minutes each using as the insect to be tested the mosquito, Aedes aegypti. The results are tabulated in Table I(A), infra.

FIG. 3B is a series of graphs depicted in three dimensions (in a rectangular mode for the "X" and "Y" axes) Showing the relative attractiveness or repellency of GERANIOL COEUR™, ISOPROXEN™, hexyl cinnamic aldehyde, opoponax absolute (defined according to the GLC spectrum of FIG. 8, infra), MARANTHA™, cis-3-hexenyl acetate, LYRAL®, GERALDEHYDE™, FLORALATE™ and air. The graphs are based on experiments run for a period of six hours with six intervals of one hour each using as the insect to be tested the mosquito, Aedes aegypti. The results are tabulated in Table I(B), infra.

Figure 21:
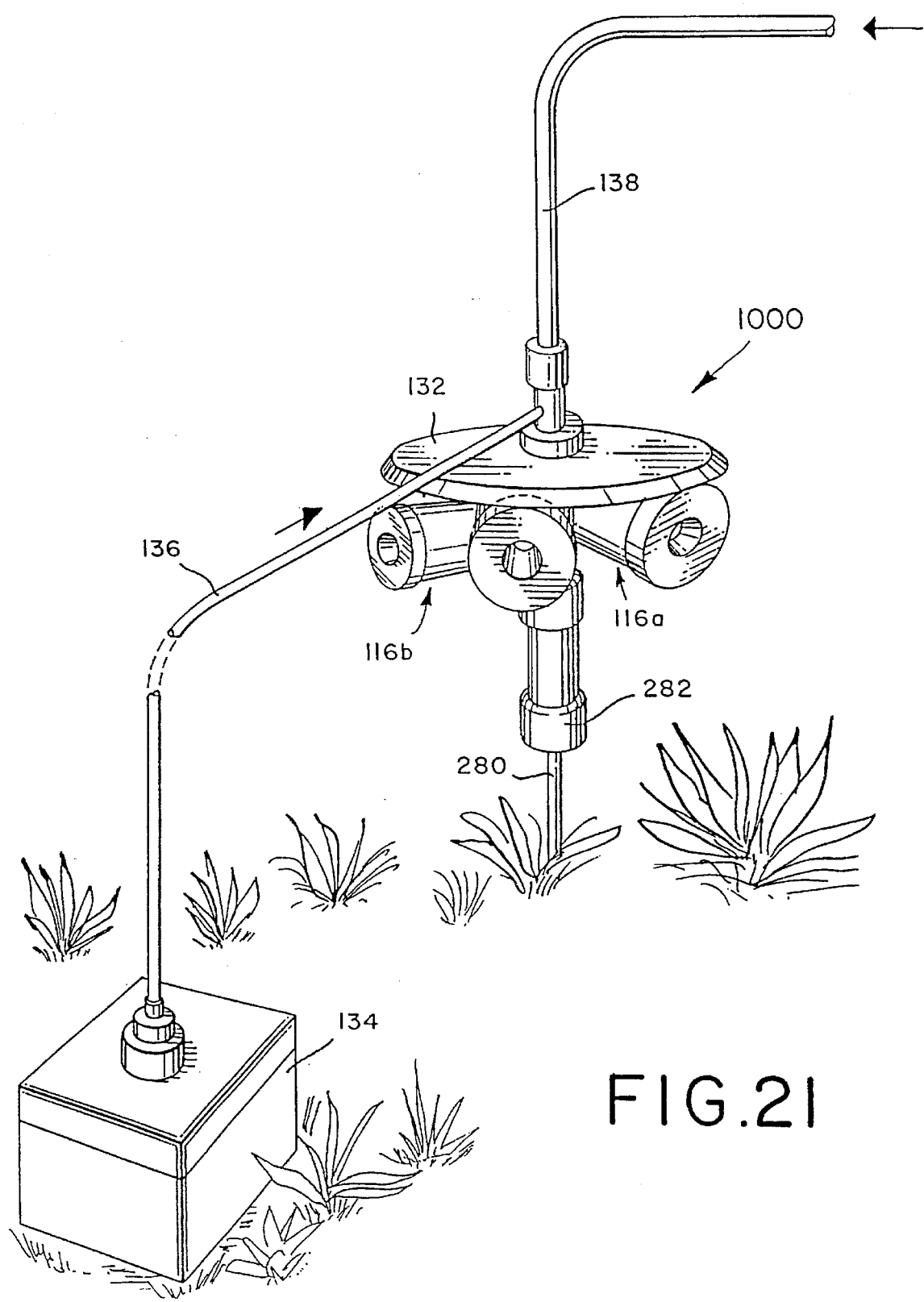

FIG. 4A is a bar graph in two dimensions showing the mean number of bites per hour by the mosquito, Aedes aegypti (on the "Y" axis) versus the treatment substance (on the "X" axis) using the semiochemical field trap of FIG. 21 with six ports and three infrared light-emitting diodes showing treatment with:

(a) ISOPROXEN™;
(b) hexyl cinnamic aldehyde;
(c) opoponax absolute as defined according to FIG. 8;
(d) MARANTHA™;
(e) cis-3-hexenyl acetate
(f) LYRAL®;
(g) GERALDEHYDE™;
(h) FLORALATE™;
(i) air; and
(j) GERANIOL COEUR™.

FIG. 4B is a bar graph showing the same results as FIG. 4A, with the exception that the graph is in three dimensions rather than two dimensions.

Figure 5:
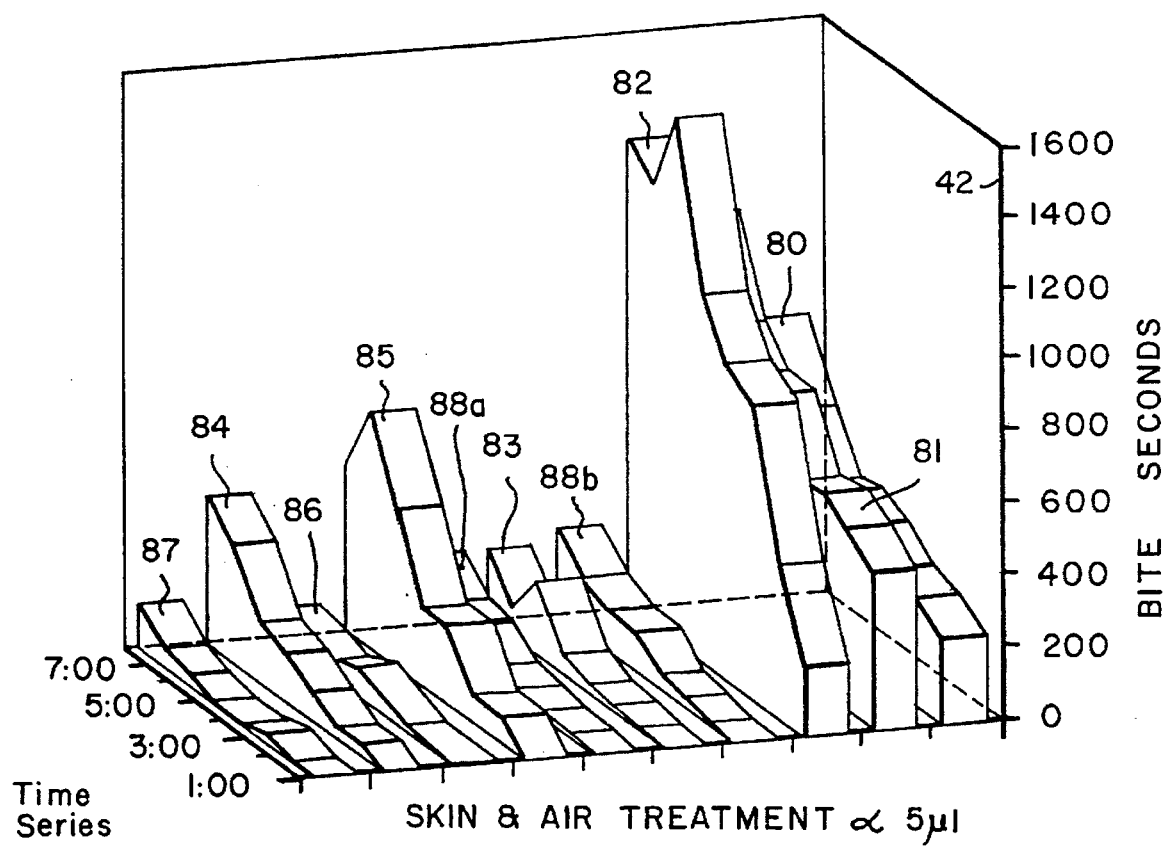

FIG. 5 is a three-dimensional bar graph showing the mean number of bite seconds by the mosquito, Aedes aegypti (on the "Y" axis) versus the treatment substance (on the "X" axis) versus the time (on the "Z" axis) using the semiochemical field trap of FIG. 21 with six ports and three infrared light-emitting diodes showing treatment with:

(a) thyme oil red (defined according to the GLC profiles of FIGS. 7A and 7B);
(b) GERALDEHYDE™;
(c) eugenol;
(d) sage oil;
(e) GERANIOL COEUR™;
(f) commercially available, floral cosmetic fragrance, "Floral No. 42A";
(g) GERANIOL COEUR™;
(h) commercially available skin conditioner "C-1F" containing bay leaf oil;
(i) glycerine; and
(j) air.

FIG. 6 is a pie chart showing the percentage of insects attracted by various treatment substances using the semiochemical field trap of FIG. 21 with six ports and three infrared light-emitting diodes, showing treatment with:

(a) thyme oil red;
(b) GERALDEHYDE™;
(c) eugenol;
(d) sage oil;
(e) GERANIOL COEUR™;
(f) commercially available, floral cosmetic fragrance, "Floral No. 42A";
(g) GERANIOL COEUR™;
(h) commercially available skin conditioner "C-1F" containing bay leaf oil;
(i) glycerine; and
(j) air.

FIG. 7A is the GLC profile for thyme oil red, one of the materials tested yielding the results set forth in FIGS. 5 and 6 described, supra (conditions: 50 meter Carbowax 20M column programmed from 70°–220° C. at 4° C. per minute).

FIG. 7B is the GLC profile for thyme oil red, which is on of the materials tested yielding the results set forth in FIGS.

5 and 6 described, supra (conditions: 50 meter OV-1 column programmed from 70°–220° C. at 4° C. per minute).

Figure 8:
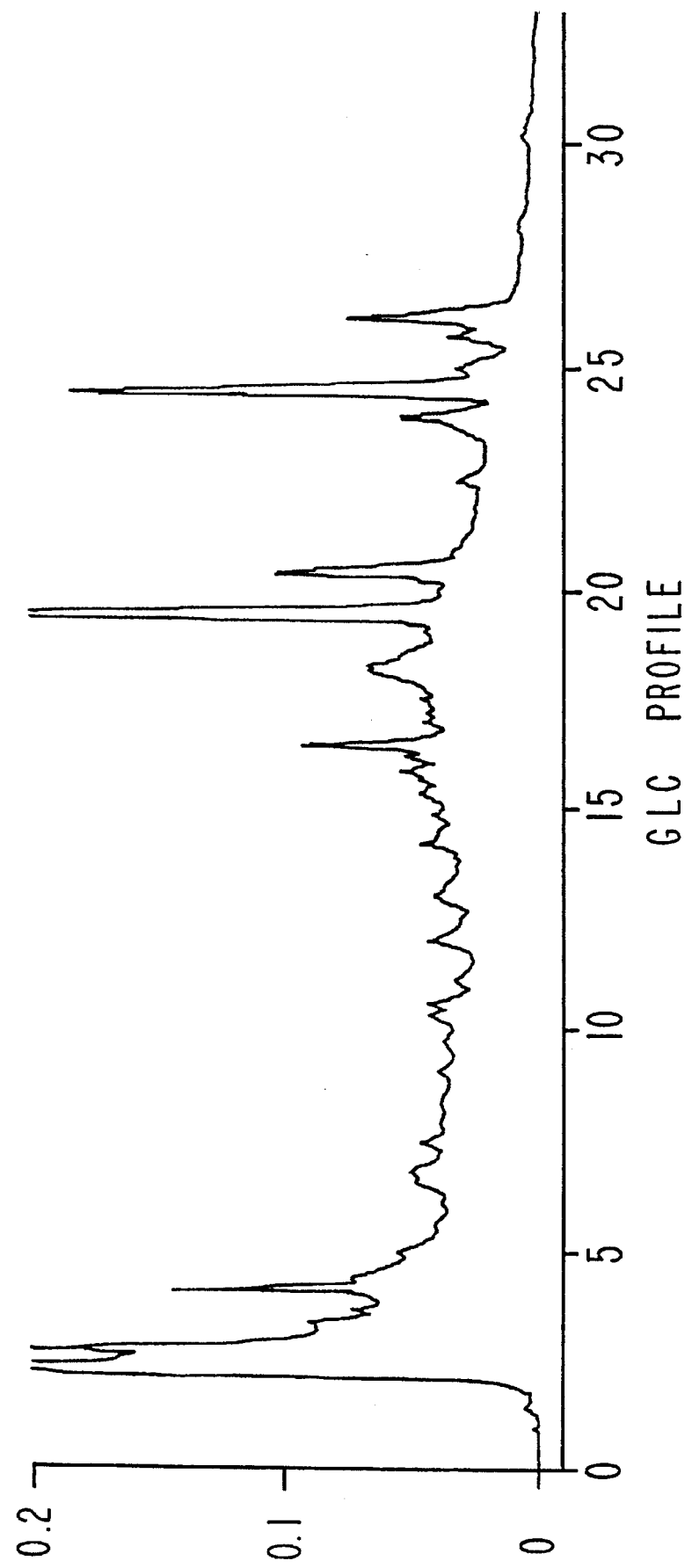

FIG. 8 is the GLC profile for opoponax absolute, one of the materials tested yielding the results set forth in FIGS. 1, 2, 3A, 3B, 4A and 4B.

Figure 9:
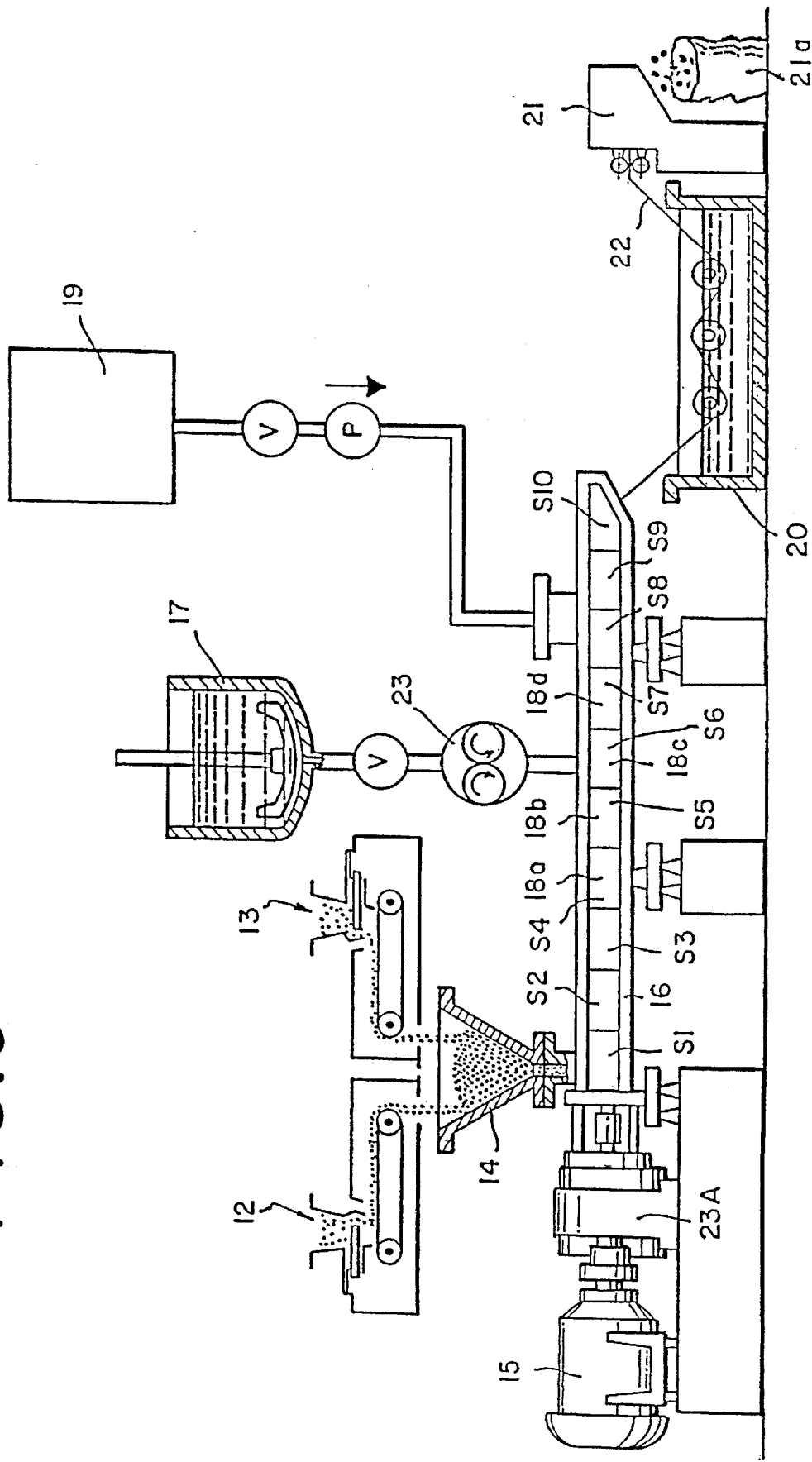

FIG. 9 is a cutaway side elevation schematic diagram of the screw extruder during the compounding of a resin with insect repellents including the unsaturated aldehyde and alkanol derivatives of our invention while simultaneously adding foaming agent into the hollow portion of the barrel of the extruder, and incorporates the pelletizing apparatus used in the pelletizing of the extruded foamed tow product produced as a result of the extrusion operation.

Figure 10:
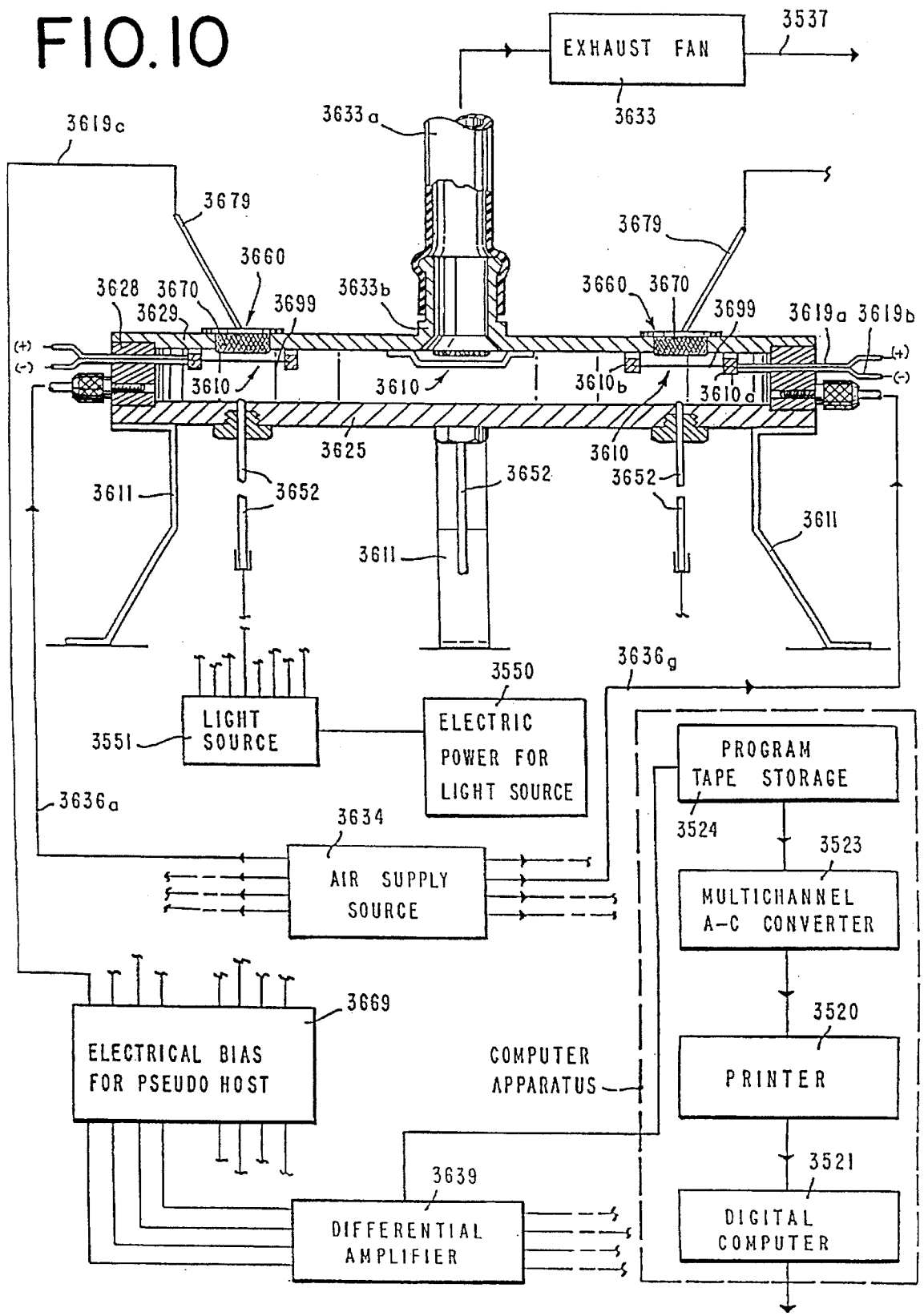

FIG. 10 is a cutaway side elevation view of the base section of the olfactometer apparatus of U.S. Pat. No. 5,134,892, the specification for which is incorporated by reference herein, used in carrying out the testing of the attractants or repellents including the repellents of our invention, indicating in schematic block flow diagram form the utilization of computer-assisted efficacy measuring apparatus; but showing only an air supply entry into the side ports of the olfactometer apparatus with the treatment agent being contained in a control release matrix upstream from the air supply source.

FIG. 11 is a perspective view of an ellipsoidally-shaped detergent tablet containing a solid core which includes fused foamed polymeric particles which contain insect repellent's which are one or more of the unsaturated aldehyde or alkanol derivatives of our invention and, if desired, also containing an additional polymer, e.g., polyethylene. The polymer particles may, if desired, also contain additional aromatizing agents.

FIG. 12 is the top view of the ellipsoidally-shaped detergent tablet of FIG. 11.

FIG. 13 is a cutaway front view of the ellipsoidally-shaped detergent tablet of FIG. 11 in the direction of the arrows in FIG. 12.

FIG. 14 is a side view of the ellipsoidally-shaped detergent tablet of FIG. 11.

FIG. 15 is a perspective view of a rectangular parallelepiped-shaped detergent tablet containing a rectangular parallelepiped-shaped core comprising a major proportion of fused foamed polymeric particles which contain insect repellents (e.g., one or more of the unsaturated aldehyde or alkanol derivatives of our invention) and may or may not be additionally aromatized and, if desired, an additional polymer which may or may not contain insect repellent compositions and which may or may not be additionally aromatized.

FIG. 16 is a top view of the rectangular parallelepiped-shaped detergent tablet of FIG. 15.

FIG. 17 is a cutaway front view of the rectangular parallelepiped-shaped tablet of FIG. 15 looking in the direction of the arrows in FIG. 16.

FIG. 18 is a perspective view of an ellipsoidally-shaped detergent tablet containing a hollow insect repellent agent (and, if desired, an additional aromatizing agent) containing core which includes fused foamed polymeric particles containing insect repellent and, if desired, additional aromatizing agent or, in the alternative, a hollow core of fused foamed polymer wherein the insect repellent which is also an aroma imparting agent (and, if desired, an additional aroma imparting agent) is in the solid polymer and not in the void of the plastic core.

FIG. 19 is a top view of the ellipsoidally-shaped detergent tablet of FIG. 18.

FIG. 20 is a front cutaway view of the ellipsoidally-shaped detergent tablet of FIG. 18 looking in the direction of the arrows in FIG. 19, the core thereof being hollow and either containing an insect repellent material of our invention (and, if desired, an additional aroma imparting liquid) or, in the alternative, being a hollow core wherein the insect repellent material of our invention (and, if desired, the additional aroma imparting material) is in the solid fused foamed polymeric particles which make up the core and wherein the void does not contain anything.

FIG. 21 is a perspective view of the semiochemical field trap for testing the attractiveness or repellency for Aedes aegypti using the unsaturated alcohol and/or alkanol derivatives of our invention. The semiochemical field trap is described in detail in U.S. Pat. No. 5,228,233 issued on Jul. 20, 1993, the specification for which is incorporated herein by reference.

FIG. 22 is the GLC profile of GERANIOL COEUR™ natural produced according to Example I, infra (conditions: dual fused silica system programmed from 70°–270° C. at 4° C. per minute).

FIG. 23 is the GLC profile for GERANIOL COEUR™ synthetic produced according to Example II, infra (conditions: dual fused silica system programmed from 70°–220° C. at 4° C. per minute).

SUMMARY OF THE INVENTION

This invention relates to the use of unsaturated aldehyde and alkanol derivatives in repelling the mosquito species, Aedes aegypti, to wit:

(i) GERANIOL COEUR™, synthetic or natural, defined according to the GLC spectra of FIGS. 22 or 23 described, supra and infra;

(ii) the mixture of compounds having the structures:

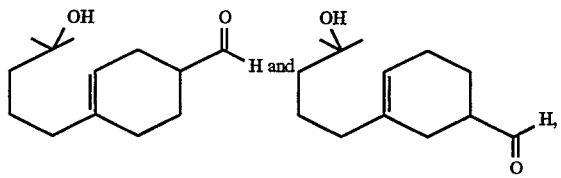

including but not limited to LYRAL®, wherein the ratio of isomers having the structures:

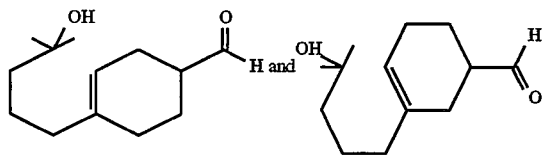

is 50:50; and (iii) GERALDEHYDE™, defined according to the structure:

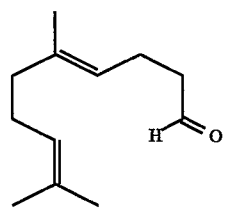

(both "cis" and "trans" isomers).

With reference to the mixture of compounds defined according to the structures:

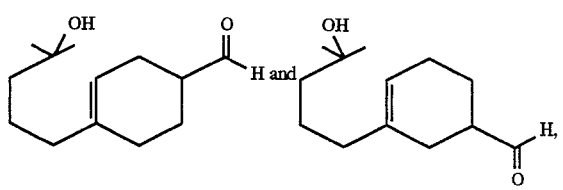

the mole ratio range of structures may vary from about 75 mole percent of the compound having the structure:

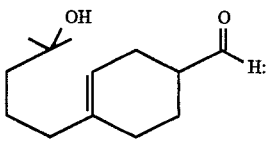

25 mole percent of the compound having the structure:

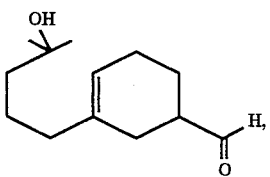

up to about 25 mole percent of the compound having the structure:

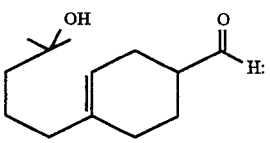

75 mole percent of the compound having the structure:

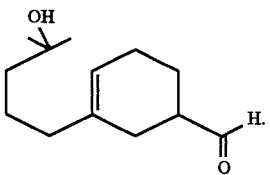

With respect to the GERALDEHYDE™ having the structure:

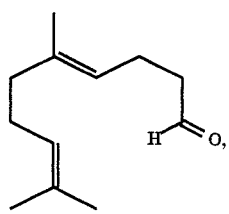

either the "cis" or the "trans" isomers of GERALDEHYDE™ are useful in the practice of our invention or mixtures of same are useful in the practice of our invention, for example, 50:50 mixtures of "cis" and "trans" GERALDEHYDE™ are useful in repelling Aedes aegypti.

Our invention also relates to the use of the foregoing insect repellent compositions in personal soap compositions, for example, the insect repellent soap composition described in U.S. Pat. No. 4,707,496 issued on Nov. 17, 1987 the specification for which is incorporated by reference herein. Thus, in applying the teachings of U.S. Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 up to 7% by weight of a soap of caprylic acid, from 3.8 up to 7% of a soap of capric acid, from 32.1 up to 45% of a soap of lauric acid, from 12 up to 17.5% by weight of a soap of myristic acid, from 5.0 up to 10% by weight of a soap of palmitic acid, from 1.6 up to 3% by weight of a soap of stearic acid, from 3.5 up to 5% by weight of a soap of oleic acid and from 0.9 up to 5% by weight of a soap of linoleic acid;

(ii) from 0.1 up to 2% by weight of $C_8$-$C_{18}$ straight chain fatty acids;

(iii) from 10 up to 30% by weight of at least one of the unsaturated aldehyde or alkanol derivative-containing compositions of our invention as set forth, supra; and (iv) from 0.2 up to 5% by weight of an effective residual insecticide as described in U.S. Pat. No. 4,707,496.

Other insect repellent soaps can be produced by adding an appropriate unsaturated aldehyde or alkanol derivative-containing composition of our invention to one or more of the compositions described and claimed in U.S. Pat. No. 4,453,909 issued on Jun. 12, 1984 and U.S. Pat. No. 4,438,010, the specifications for which are incorporated by reference herein. Described in said U.S. Pat. No. 4,453,909 and U.S. Pat. No. 4,438,010 is a process for making a tablet of soap containing a perfume-containing core, hollow or solid fabricated from a hard plastic material either thermosetting or thermoplastic. The soap from the resulting composite tablet is usable until the core is washed clean and contains functional ingredients, e.g., the repellents described, supra, and, optionally, an aromatizing agent until the core is washed clean. This obviates the wastage of soap which normally occurs as a conventional soap tablet becomes very thin on use and at the same time gives rise to a continuously functional ingredient containing soap (e.g., a repellent and optionally aromatizing agent) tablet. Thus, this invention also relates to detergent bars having a plastic core containing an appropriate unsaturated aldehyde or alkanol derivative-containing composition and, optionally, an additional perfume. More particularly, this invention relates to detergent bars intended for conventional toilet soap uses either as hand soaps or bath or shower soaps which are elastic or inelastic in nature but which contain a solid plastic core containing insect repellent and, optionally, perfume, giving them unique properties which alleviate wastage thereof and causes the environment surrounding the soap on use thereof to be both insect repellent and, optionally, aromatized in an aesthetically pleasing manner.

Yet another aspect of our invention relates to the use of the unsaturated aldehyde or alkanol derivative-containing repellents of our invention taken further in combination with N-(methyl toluyl)-methylpiperidines defined according to the structure:

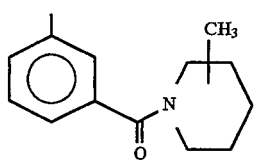

as described in U.S. Pat. No. 3,463,855 issued on Aug. 26, 1969 the specification for which is incorporated by reference herein. The compounds defined according to the structure:

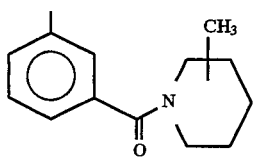

include:
N-(meta-toluyl)-2-methylpiperidine;
N-(meta-toluyl)-3-methylpiperidine; and
N-(meta-toluyl)-4-methylpiperidine.

The proportions of compounds defined according to the structure:

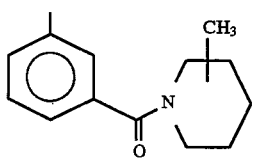

to the appropriate unsaturated aldehyde or alkanol derivative-containing composition described, supra, are between 1 part N-(meta-toluyl) methylpiperidine:99 parts of appropriate unsaturated aldehyde or alkanol derivative-containing composition of our invention down to 99 parts of appropriate unsaturated aldehyde or alkanol derivative-containing composition of our invention:1 part N-(metatoluyl)-methylpiperidines.

In addition, the compositions of our invention useful in repelling insects can also contain 1-nonen-3-ol described and claimed in U.S. Pat. Nos. 4,693,890 and 4,759,228 issued on Jul. 26, 1988 the specifications for which are incorporated by reference herein. The ratio of 1-nonen-3-ol:appropriate unsaturated aldehyde or alkanol derivative-containing composition of our invention useful in repellent compositions may vary from about 1 part 1-nonen-3-ol:99 parts appropriate unsaturated aldehyde or alkanol derivative-containing composition of our invention down to 99 parts 1-nonen-3-ol:1 part appropriate unsaturated aldehyde or alkanol derivative-containing composition of our invention.

In addition to the soap fabrication, another aspect of our invention relates to the formation of repelling articles containing the appropriate unsaturated aldehyde or alkanol derivative-containing compositions of our invention, that is, articles useful for repelling the mosquitoes (*Aedes aegypti*) in combination with compatible polymers which may or may not be biodegradable (for example, high density polyethylene or low density polyethylene, or biodegradable polymers such as biodegradable thermoplastic polyurethanes as disclosed in Japan Kokai Tokyo Koho 92/13710 (abstracted at *Chemical Abstracts*, Volume 116:236397z), biodegradable ethylene polymers having ester linkages in the main chain such as that disclosed by Japan Kokai Tokyo Koho 92/50224 (abstracted at *Chemical Abstracts*, Volume 116:126397z); biodegradable ethylene polymers disclosed by Japan Kokai Tokyo Koho 92/50225 (abstracted at *Chemical Abstracts*, Volume 116:126398a; and poly(epsilon caprolactone) homopolymers and compositions containing same as disclosed in U.S. Pat. Nos. 4,496,467; Nos. 4,469,613 and 4,548,764, the specifications for which are incorporated herein by reference. Thus, another aspect of our invention provides a process for forming appropriate unsaturated aldehyde or alkanol derivative-containing compositions containing polymeric particles such as foamed polymeric pellets which include a relatively high concentration of the appropriate unsaturated aldehyde or alkanol derivative-containing compositions of our invention as defined, supra.

Thus, another aspect of our invention relates to the formation of appropriate unsaturated aldehyde or alkanol derivative-containing polymeric pellets by means of introduction into a single or twin screw extruder, in series, a thermoplastic polymer followed by the appropriate unsaturated aldehyde or alkanol derivative-containing composition of our invention which is compatible with the thermoplastic polymer, in turn (optionally), followed by introduction of a gaseous blowing agent or blowing agent which will produce a gas which is inert to the polymer and to the appropriate unsaturated aldehyde or alkanol derivative-containing composition previously introduced into the extruder.

The advantage of using a foamed polymeric particle are multiple, to wit:

(i) improved handling;

(ii) greater retention of the appropriate unsaturated aldehyde or alkanol derivative-containing composition when not in use; and (iii) greater length of time during which the release of the appropriate unsaturated aldehyde or alkanol derivative-containing composition of our invention from the polymer is at "steady state" or "0 order".

The nature of the extruder utilized in the process of our invention to form the appropriate unsaturated aldehyde or alkanol derivative-containing, composition containing polymer particles of our invention may be either single screw or double screw. Thus, the types of extruder that can be used are disclosed at pages 246–267 and 332–349 of the *Modern Plastics Encyclopedia*, 1982–1983, published by the McGraw-Hill Publishing Company, the disclosure of which is incorporated by reference herein. More specifically, examples of extruders which are usable in carrying out one or more of the processes of our invention (with modification for introduction of the appropriate unsaturated aldehyde or alkanol derivative-containing compositions of our invention) downstream from the introduction of the polymer and with further modification that the gaseous blowing agent is introduced still further downstream from the point of introduction of the appropriate unsaturated aldehyde or alkanol derivative-containing compositions of our invention are as follows:

1. The Welex "Super Twinch" 3.5 inch extruder manufactured by Welex Incorporated, 850 Jolly Road, Blue Bell, Pa. 19422;

2. Krauss-Maffei twin screw extruder manufactured by the Krauss-Maffei Corporation/Extruder Division, 3629 West 30th Street South, Wichita, Kans. 67277;

3. Modified Sterling Model 4000 and 5000 series extruder manufactured by Sterling Extruder Corporation of 901 Durham Avenue, South Plainfield, N.J.;

4. CRT ("Counter-Rotating Tangential") Twin Screw Extruder manufactured by Welding Engineers, Inc. of King of Prussia, Pa. 19406;

5. The Leistritz Twin Screw Dispersion Compounder manufactured by the American Leistritz Extruder Corporation of 198 U.S. Route 206 South, Somerville, N.J. 08876;

6. The ZSK Twin Screw Co-Rotating Extruder manufactured by the Werner & Pfleiderer Corporation of 663 East Crescent Avenue, Ramsey, N.J. 07446;

7. The Farrel Extruder manufactured by Farrel Connecticut Division, Emhart Machinery Group, Ansonia, Conn. 06401;

8. The MPC/V Baker Perkins Twin Screw Extruder manufactured by the Baker Perkins Inc. Chemical Machinery Division of Saginaw, Mich. 48601; and 9. The Berstorff single screw, twin screw or foam extrusion equipment manufactured by Berstorff Corporation, P.O. Box 240357, 8200-A Arrowing Boulevard, Charlotte, N.C. 28224.

In producing the appropriate unsaturated aldehyde or alkanol derivative-containing composition containing polymer particles of our invention, various polymers may be utilized, for example, low density polyethylene, high density polyethylene, polypropylene, the copolymer of ethylene and vinyl acetate, and polyvinyl chloride. More specifically, the polymers used in the practice of our invention may be copolymers of ethylene and a polar vinyl monomer selected from (a) vinyl acetate; (b) ethyl acrylate; (c) methyl acrylate; (d) butyl acrylate; and (e) acrylic acid including the hydrolyzed copolymer of ethylene and vinyl acetate. Preferred copolymers are ethylene/vinyl acetate with about 9 to 60% vinyl acetate and ethylene/ethyl acrylate with about 6 to 18% ethyl acrylate.

Resins of the type disclosed for use as copolymers are commercially available in the molding powder form; for example, ethylene vinyl acetate copolymers are marketed by the E. I. dupont Nemours Company under the Tradename ELVAX® and by the Arco Polymer Division under the Trademark DYLAND® and by the Exxon Corporation of Linden, N.J. under the Trademark DEXXON®. Ethylene/ethyl acrylate copolymers are marketed by Union Carbide Corporation under the Trademark EEA RESIN®.

The polymer is added to the single screw or twin screw extruder at a feed rate in the range of from about 80 up to about 300 pounds per hour while maintaining the temperature of the screw extruder between about 160° C. and about 240° C. If the polymer or copolymer powder is added to the extruder at a reference "barrel segment" then the appropriate unsaturated aldehyde or alkanol derivative-containing composition of our invention is added to the extruder under pressure downstream from the retention point of the polymer at one or more of the "barrel segments" (S-2, S-3, S-5, S-6, S-7, S-8 or S-9) (referring to FIG. 9 briefly described, supra, and described in detail, infra).

The proportion of the appropriate unsaturated aldehyde or alkanol derivative-containing composition (taken further together with other insect repelling materials, if desired) to resin can vary from small but effective amounts on the order of about 1% of the weight of the resin body up to about 45% by weight of the resin body. In general, it is preferred to use between about 5% up to about 30% based on the weight of the resin body of insect repellent composition of our invention. This is an optimum amount balancing the proportion of the insect repellent composition of our invention against the time period over which the article emits the insect repellent composition and against the tendency of the components of the insect repellent composition to oil out either individually or in combination. This "oiling out" is specifically avoided as a result of the use of the foaming agent discussed, infra.

Various polymers are useful in the practice of our invention. Specific examples of polymers useful in the practice of our invention are as follows:

(a) DYLAN® brand of low density polyethylene, DYLAN® is a trademark owned by the Atlantic Richfield Company of Los Angeles, Calif.;

(b) DYLITE® of expandable polystyrene composition, DYLITE® is a trademark of the Atlantic Richfield Company of Los Angeles, Calif.

(c) SUPER DYLAN® is a trademark of the Atlantic Richfield Company of Los Angeles, Calif.;

(d) blended polyethylene and carbon black as specifically taught in U.S. Pat. No. 4,369,267 issued on Jan. 18, 1983 the specification for which is incorporated by reference herein;

(e) polystyrene as disclosed in U.S. Pat. No. 4,369,227 issued on Jan. 18, 1983 the specification for which is incorporated by reference herein;

(f) polyene/α-olefin as exemplified and disclosed in U.S. Pat. No. 4,369,291 the specification for which is incorporated by reference herein;

(g) poly-α-olefins disclosed in Canadian Letters Patent No. 1,137,069 issued on Dec. 7, 1982 the specification for which is incorporated by reference herein;

(h) polymeric compositions as disclosed in Canadian Letters Patent No. 1,137,068 issued on Dec. 7, 1982 the specification for which is incorporated by reference herein;

(i) poly-α-olefins disclosed in Canadian Letters Patent No. 1,137,067 the specification for which is incorporated by reference herein;

(j) polyolefins described in Canadian Letters Patent No. 1,137,066 the specification for which is incorporated by reference herein;

(k) polyethylene oxides as disclosed in Canadian Letters Patent No. 1,137,065 issued on Dec. 7, 1982 the specification for which is incorporated by reference herein;

(l) olefin polymers and copolymers as disclosed in Canadian Letters Patent No. 1,139,737 issued on Jan. 18, 1983 the disclosure of which is incorporated by reference herein;

(m) polyolefins disclosed in Canadian Letters Patent No. 1,139,738 issued on Jan. 18, 1983 the disclosure of which is incorporated by reference herein;

(n) chlorinated PVC as disclosed in *Polymer* 1982, 23 (7, Suppl.), pages 1051–5, abstracted at *Chemical Abstracts*, Volume 97:14550y, 1982;

(o) polyepsilon caprolactone copolymers made by means of alcohol initiated polymerization as disclosed in *J. Polym. Sci. Polym. Chem. Ed.* 1982, 20 (2), pages 319–26, abstracted at *Chemical Abstracts*, Volume 96:123625x, 1982;

(p) styrene acrylonitrile copolymers as disclosed in *Diss. Abstracts Int. B*, 1982, 42 (8), page 3346 and abstracted at *Chemical Abstracts*, Volume 96:143770n, 1982;

(q) copolymers of epsilon caprolactone with 1,4-butane diol as disclosed in Kauch Rezine, 1982, (2), pages 8–9, abstracted at *Chemical Abstracts*, Volume 96:182506g, 1982;

(r) polyesters as disclosed in U.S. Pat. No. 4,326,010 the specification for which is incorporated by reference herein;

(s) chlorinated polyethylene as disclosed by Belorgey, et al, *J. Polym. Sci. Plym. Ed.* 1982, 20 (2), pages 191–203;

(t) plasticized polyepsilon caprolactone copolymers containing dimethyl phthalate plasticizers as set forth in Japanese Patent No. J81/147844, abstracted at *Chemical Abstracts*, Volume 96:669984y, 1982, the specification for which is incorporated by reference herein;

(u) maleic anhydride modified adducts of polyepsilon caprolactone polyols and ethylenically unsaturated monomer as disclosed in U.S. Pat. No. 4,137,279 issued on Jan. 30, 1979 the specification for which is incorporated by reference herein;

(v) polyurethane polymers having lactone backbones as disclosed in U.S. Pat. No. 4,156,067 issued on May 22, 1979 the disclosure of which is incorporated by reference herein;

(w) polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981 the disclosure of which is incorporated by reference herein; and (x) resins having polyurethane backbones as disclosed in U.S. Pat. No. 3,975,350 issued on Aug. 17, 1976 the disclosure of which is incorporated by reference herein.

Examples of poly(epsilon caprolactone) homopolymers as set forth, for example, in U.S. Pat. No. 4,496,467 are those having the structures:

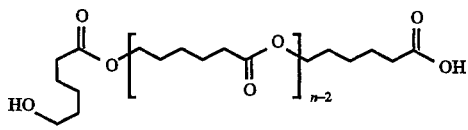

and

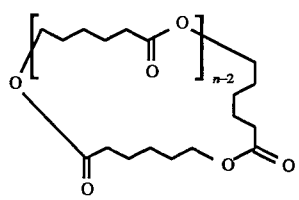

wherein n represents an integer of from about 500 up to about 1,200 with the proviso that the average "n" varies from about 600 up to about 800.

Downstream from the addition point of the unsaturated aldehyde or alkanol derivative-containing compositions of our invention taken alone or taken together with other insect repellent agents and fragrance materials, optionally, the gaseous liquid containing blowing agent may be added (e.g., at "barrel segments" S-5, S-6, S-7, S-8, S-9 or S-10) using the polymer addition "barrel segment" as a reference "barrel segment" S-1. Examples of the gaseous blowing agents are carbon dioxide in proportions of from 1 up to 99% by volume nitrogen and from 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 to about 150 psig. Higher pressure may be used without adversely affecting the usefulness of the foamed insect repellent composition-containing particle.

The feed rate range of insect repellent compositions which contain but which are not limited to the unsaturated aldehyde or alkanol derivative-containing compositions of our invention may be between about 0.5% up to about 45% by weight of the polymer. It must be emphasized at this point that the insect repellent composition of our invention which are the unsaturated aldehyde or alkanol derivative-containing compositions of our invention are in and of themselves aromatizing materials. However, the maximum quantity of the combination of other aromatizing materials and the appropriate unsaturated aldehyde or alkanol derivative-containing compositions of our invention is 45%.

The dies of the extruder may create rod, sheet, film or ribbon. The resulting product may then, if desired, be pelletized to form insect repellent composition-containing polymer particles or the ribbon may be used "as is" as an insect repellent-containing polymeric article of manufacture itself.

In addition to the optional gaseous blowing agents (which are necessarily "inert" gases), blowing agents may be added at the same point on the extruder which will create gaseous voids in the insect repellent-containing polymer articles of our invention and these "blowing agents" are well known to one having ordinary skill in the art. Examples of such non-gaseous containing materials which yield gases on admixture with the polymer in the extruder but which are still inert to the insect repellent are as follows:

(i) under high pressure, ethylene, methane, propane, butane, propylene, methyl chloride, methyl bromide, vinyl chloride and methylene dichloride as more specifically described in U.S. Pat. No. 2,387,730 the specification for which is incorporated by reference herein;

(ii) ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5 the specification for which is incorporated by reference herein;

(iii) dichlorotetrafluoromethane, tetramethylmethane, monochlorodifluoromethane, dichlorodifluoromethane and dichlorotetrafluoromethane as described in U.S. Pat. Nos. 2,948,664 and 2,948,665 issued on Aug. 9, 1990 the specifications for which are incorporated by reference herein; and (iv) azo bis(formamide), diazoaminobenzene; N,N-dinitrosopentamethylene tetramine; N,N-dimethyl, N,N-dinitrosoterephthalamide; p,p'-oxy-bis-(benzene sulfonyl semicarbazide); aza bis-(isobutyronitrile)p,p'-oxy'bis(benzene sulfonyl hydrazide); p,p'-diphenyl-bis (sulfonyl hydrazide); benzene-sulfonyl hydrazide; m-benzene-bis(sulfonyl hydrazide) as more specifically described in U.S. Pat. No. 3,298,975 issued on Jan. 17, 1967 the specification for which is incorporated by reference herein.

The resulting extruded (and, if desired, pelletized) material may then be, for example, injection molded to form a useful article. Such injection molding can be carried out in accordance with the procedure as set forth in U.S. Pat. No. 3,268,636 issued on Aug. 23, 1966 the specification for which is incorporated by reference herein.

In addition, our invention relates to candle body materials which on use are both insect repellent and perfuming which contain the appropriate unsaturated aldehyde or alkanol derivative-containing compositions of our invention and, if desired, other insect repellent materials including, for example, at least one of the compounds having the structure:

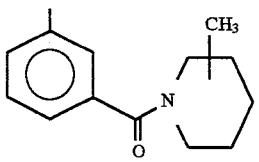

in order to repel the mosquitoes, Aedes aegypti.

The mosquito repellent-perfuming compositions which form part of the candle body materials are within the following specifications:

(i) from 5 up to 100% by weight of an efficacious perfuming/insect repellent composition containing an appropriate unsaturated aldehyde or alkanol derivative-containing composition of our invention; and (ii) from 0 up to 95% by weight of an additional standard perfuming substance (non-insect repellent or insect repellent) which may include but is not limited to:
1-nonen-3-ol;
1-octen-4-ol;
α-damascone;
β-damascone;
δ-damascone;
trans, trans δ-damascone;
methyl jasmonate;
dihydromethyl jasmonate;
the schiff base of vanillin and methyl anthranilate;
the schiff base of ethyl vanillin and methyl anthranilate;
vanillin; and
ethyl vanillin.

The foregoing formula may require a solubilizing agent, e.g., the methyl ester of dihydroabietic acid (commercial name: HERCOLYN® D), benzyl benzoate, isopropyl myristate and/or $C_{12}$–$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;

(ii) an alkanol amide or alkanol amine; and (iii) a stearic acid compound.

The weight ratio of candle body:insect repellent/ perfumant substance or our invention may vary from about 0.8% up to about 10% with a range of from about 0.8% up to about 2.0% being preferred when no additional non-insect repelling perfume oil is used in conjunction with the appropriate unsaturated aldehyde or alkanol derivative-containing composition of our invention; and with a range of from about 1.5% up to about 10% by weight of the overall composition being preferred when an additional non-insect repelling perfume oil is used in conjunction with the appropriate unsaturated aldehyde or alkanol derivative-containing composition of our invention.

Specifically, the polyamide may be a VERSAMID® resin which is a thermoplastic condensation product of polymerized linoleic acid with various polyamine compounds such as ethylene diamine, ethylene triamine and the like. Specific VERSAMID® compounds are VERSAMID® 900, VERSAMID® 930, VERSAMID® 940, VERSAMID® 948, VERSAMID® 950 and VERSAMID® 1635. These compounds are products of the Henkel Chemical Corporation of Minneapolis, Minn.

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as BARLOL® 12C2 (manufactured by the Baroid Chemical Company) a monoalkyl diethanolamine having 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. The stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection, it is possible to use up to about 10% by weight of a perfumant/insect repellent if part of the formula is replaced by the material NEVEX® 100, a product which is a coumarin-indene copolymer resin of very little unsaturation manufactured by the Neville Chemical Company.

Rather than being a crystalline paraffin wax, the candle base of our invention may be an oil gel that has as its base a light mineral oil, an inexpensive natural oil or a combination of such oils which oil gel has a non-greasy surface and feel and sufficient rigidity to be self-supporting at room temperature. Such a gel is disclosed in U.S. Pat. No. 3,645,705 issued on Feb. 29, 1972 the disclosure of which is incorporated by reference herein. Such compositions of matter include:

(a) from about 35% up to about 85% by weight of an oil which is normally liquid at room temperature chosen from the group consisting of light mineral oils and natural oils having iodine values substantially within the range of 40–135;

(b) from about 7% up to about 40% by weight of a long chain polyamide having a molecular weight substantially within the range of 6,000–9,000 and a softening point substantially within the range of 18° C.–48° C.; and (c) from about 7% up to about 30% of alcohol selected from the group consisting of 8 to 12 carbon primary alcohols.

DETAILED DESCRIPTION OF THE DRAWINGS

The data set forth in FIGS. 1, 2, 3A, 3B, 4A, 4B, 5 and 6 were determined using the olfactometer of FIG. 10 and the insect trap of FIG. 21.

Referring to the olfactometer of FIG. 10, said olfactometer is described in detail in U.S. Pat. No. 5,118,711 issued on Jun. 2, 1992 the specification for which is incorporated by reference herein.

Referring to FIG. 10, air supply source 3634 provides air to mixing station 3636 wherein the air is mixed with treatment agent from treatment agent source 3635 (source of, for example, the repellent composition which is an appropriate unsaturated aldehyde or alkanol derivative-containing composition). The resulting mixture passes through the tube 3636g and enters the apparatus through the side portals. The entry is through a spacer plate and above base plate 3625. The entry of the air-treatment agent is in a direction parallel to the surface of base plate 3625. Thus, the base plate 3625 is separated from spacer plate 3629 for the air-treatment agent (e.g., the appropriate unsaturated aldehyde or alkanol derivative-containing composition of our invention).

Air exits through line 3533a using exhaust fan 3633. The air exit is indicated by reference numeral 3537.

Simultaneously, with the supplying of air and treatment agent from mixing station 3636, light is supplied from beneath the enclosed insect feeding and/or stimulating means through light guides 3652 from light source 3551 which is powered by electric power supply 3550 marketed by RADIO SHACK®, Division of Tandy Corporation of Forth Worth, Tex. 76102 under the Trademark ARCHER®, Catalog No. 276-228 ("1.0 mm optical plastic fiber length 5 meter"). An example of light source 3551 is KRATOS® Monochromator Illuminator GM 100 Miniature VIS-IR Grating Monochromator (Model No. GM 100-1, GM 100-2, GM 100-3 or GM 100-4) as manufactured by KRATOS® Analytical Instruments Corporation, 170 Williams Drive, Ramsey, N.J. 07446. Another light supply source is the KRATOS® GM 200 Double Grating Monochromator. Another example of a useful light source is the KRATOS® GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source from location 3634 and treatment agent from location 3635 is mixed at mixing station 3636 whereupon treatment agent and air in admixture is passed through lines 3636a and 3636g through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628. It should be noted that the spacer plate 3629, spacer ring 3628 and base plate 3625 enclose the entire "enclosed insect feeding and/or stimulating means" which have controlled limited access to the external environment surrounding the apparatus and in which the insects to be tested, e.g., mosquitoes.

The insect attractant quantitative detecting means made up of wires 3699 (the entire grid being denoted using reference numeral 3610) is located immediately beneath the porous membrane 3670, the outer surface of which contains a feeding stimulant composition or stimulant composition for insects (for example, agar). Immersed in the feeding stimulate composition or stimulant composition for insects (e.g., agar) is electrode 3679 connected to wire 3619 which connects with either wire 3619a or 3619b which is connected to the grid wires 3699 (which make up the insect attractant quantitative detecting means located immediately below lamina 3670).

As stated, supra, the sensor causes an electrical impulse caused by the pressure of the insects landing to proceed through wires 3619a and 3619b to an electrically biased differential amplifier 3639 (using electrical power supply 3539) also connected to wire 3619c which is connected to the electrode 3679 which is immersed in the feeding stimulant composition or stimulant for the insect and then to a multi-channel A.C. converter 3523. Converter 3523 is associated with program tape storage 3524, printer 3520 and data link to digital computer 3521 Differential amplifier 3639 is connected in series to electrical bias for pseudo host 3669 which in turn is connected to wire 3619 which in turn is connected to the electrode 3679 immersed in the insect stimulant composition located on the surface of porous lamina 3670.

Referring to the testing apparatus, the semiochemical field trap 1000 for blood feeding arthropods, field trap 1000 is located in a three-space with axes perpendicular to one another. The semiochemical field trap 1000 is shown in perspective view in FIG. 21 comprising:

(1) an upright, vertically disposed housing;

(2) extending outwardly from the housing a plurality of horizontally disposed hollow housings 116a and 116b which have contained therein insect sticky traps;

(3) air 138 and/or carbon dioxide supply means 134 and 136 for supplying air and/or carbon dioxide into the vertical hollow housing and then through the plurality of horizontally disposed hollow housings 116a and 116b; and (4) at least one power supply means for energizing radiation means located on the vertical hollow housing whereby on engagement of the power supply means with the radiation means and operation of the air 138 and/or carbon dioxide supply means 134 and 136, arthropods in the vicinity of the trap are attracted by the activated radiation means and the gas emanating from the horizontally disposed hollow housing 116a to a location so close to the trap 1000 that in the event that an attracting semiochemical located in the housings of 16a and 116b is detected by at least one of the arthropods, at least one of the arthropods will enter the inner void of the horizontally disposed hollow housings 116a and 116b counter current the gas stream emanating therefrom and remain permanently entrapped therein.

The semiochemical field trap 1000 of FIG. 21 is disclosed in detail in U.S. Pat. No. 5,228,233 issued on Jul. 20, 1993, the specification for which is incorporated by reference herein.

Figure 1:
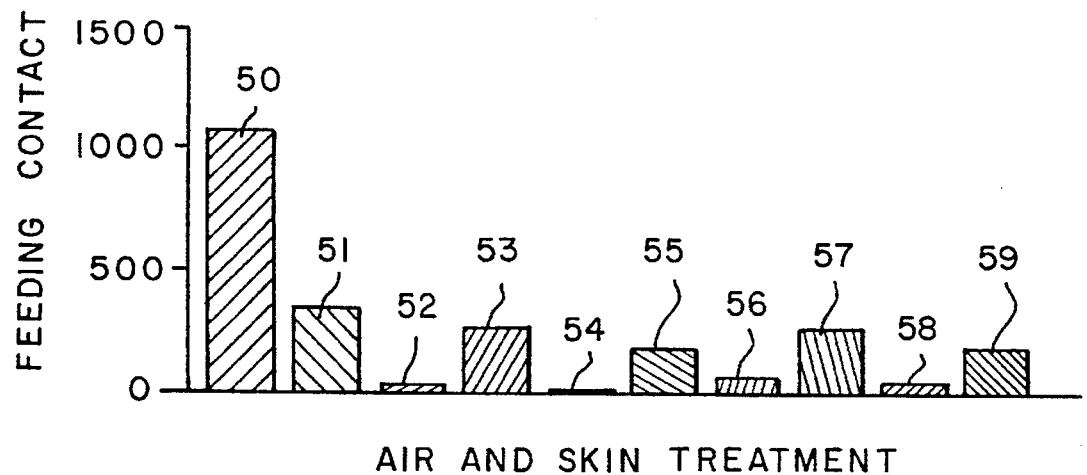
FIG. 1 is a bar graph showing the mean number of feeding contacts (on the "Y" axis) versus the particular treatment substance (on the "X" axis) for air, hexyl cinnamic aldehyde having the structure.

FIG. 1 is a bar graph showing the mean number of feeding contacts (on the "Y" axis) versus the particular treatment substance (on the "X" axis) for a mean feeding contact time of one hour. The bar graph indicated by reference numeral 50 is for air. The bar graph indicated by reference numeral 51 is for hexyl cinnamic aldehyde having the structure:

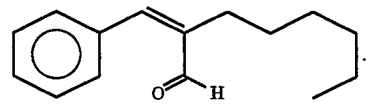

The bar graph indicated by reference numeral 52 is for LYRAL®, a 50:50 mixture of the compounds having the structures:

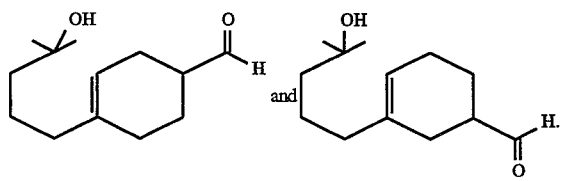

The bar graph indicated by reference numeral 53 is for FLORALATE™ having the structure:

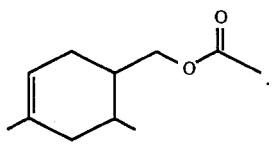

The bar graph indicated by reference numeral 54 is for GERALDEHYDE™ having the structure:

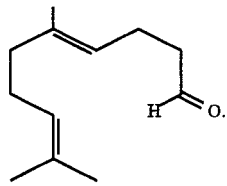

The bar graph indicated by reference numeral 55 is for ISOPROXEN™, a 50:50 mixture of compounds having the structures:

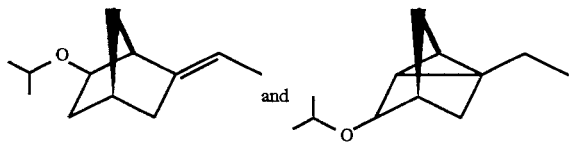

The bar graph indicated by reference numeral 56 is for opoponax oil, described by Arctander, Perfume and Flavor Materials of Natural Origin, published in 1960 by the author, at column 471, incorporated herein by reference. The bar graph indicated by reference numeral 57 is for cis-3-hexenyl acetate having the structure:

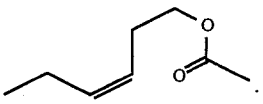

The bar graph indicated by reference numeral 58 is for GERANIOL COEUR™ natural produced according to the process of Example I and defined according to the GLC profile of FIG. 22. The bar graph indicated by reference numeral 59 is for MARANTHA™ having the structure:

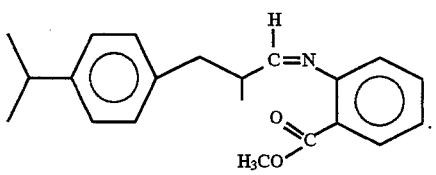

The ISOPROXEN™, indicated by reference numeral 55 in the bar graph, is prepared according to Example I of U.S. Pat. No. 4,330,416 issued on May 18, 1982 the specification for which is incorporated by reference herein.

FIG. 2 is a bar graph showing the mean number of feeding contacts (on the "Y" axis) versus the particular treatment substance (on the "X" axis) for a mean 2–6 hour feeding contact time. The bar graph indicated by reference numeral 50' is for air. The bar graph indicated by reference numeral 51' is for hexyl cinnamic aldehyde. The bar graph indicated by reference numeral 52' is for LYRAL®. The bar graph indicated by reference numeral 53' is for FLORALATE™. The bar graph indicated by reference numeral 54' is for GERALDEHYDE™. The bar graph indicated by reference numeral 55' is for ISOPROXEN™. The bar graph indicated by reference numeral 56' is for opoponax oil. The bar graph indicated by reference numeral 57' is for cis-3-hexenyl acetate. The bar graph indicated by reference numeral 58' is for GERANIOL COEUR™ natural prepared according to Example I and defined according to the GLC spectrum of FIG. 22. The bar graph indicated by reference numeral 59' is for MARANTHA™.

The data supporting the foregoing bar graphs is obtained by use of the apparatus of FIG. 10.

The following Table A sets forth the experimental mosquito (Aedes aegypti) feeding contact results which generated the graphs of FIGS. 1 and 2. The data in Table A is for FIG. 1. The data in Table B is for FIG. 2:

TABLE A

| | | Insects Collected Per Interval | | | |
|---|---|---|---|---|---|
| Treatment Agent | Graph Reference Numeral | Interval Lengths of from 0–15 Minutes | Interval Lengths of from 15–30 Minutes | Interval Lengths of from 30–45 Minutes | Interval Lengths of from 45–60 Minutes |
| Air | 50 | 1379 | 1022 | 753 | 1185 |
| Hexyl cinnamic aldehyde | 51 | 714 | 116 | 391 | 180 |
| LYRAL ® | 52 | 34 | 27 | 47 | 0 |
| FLORALATE ™ | 53 | 1 | 15 | 1038 | 12 |
| GERALDEHYDE ™ | 54 | 8 | 19 | 2 | 12 |
| ISOPROXEN ™ | 55 | 103 | 161 | 457 | 65 |
| Opoponax oil | 56 | 97 | 9 | 162 | 2 |
| Cis-3-hexenyl acetate | 57 | 802 | 60 | 87 | 163 |
| GERANIOL COEUR ™ | 58 | 1 | 2 | 132 | 24 |
| MARANTHA ™ | 59 | 541 | 222 | 7 | 13 |

TABLE B

| | | Insects Collected Per Interval | | | |
|---|---|---|---|---|---|
| Treatment Agent | Graph Reference Numeral | Interval Lengths of from 2–3 Hours | Interval Lengths of from 3–4 Hours | Interval Lengths of from 4–5 Hours | Interval Lengths of from 5–6 Hours |
| Air | 50' | 1088 | 1233 | 719 | 709 |
| Hexyl cinnamic aldehyde | 51' | 419 | 82 | 318 | 211 |
| LYRAL ® | 52' | 267 | 21 | 26 | 10 |
| FLORALATE ™ | 53' | 1 | 9 | 1055 | 28 |
| GERALDEHYDE ™ | 54' | 8 | 19 | 3 | 6 |
| ISOPROXEN ™ | 55' | 615 | 393 | 163 | 271 |
| Opoponax oil | 56' | 54 | 15 | 43 | 25 |
| Cis-3-hexenyl acetate | 57' | 945 | 782 | 184 | 192 |
| GERANIOL COEUR ™ | 58' | 0 | 0 | 2 | 0 |
| MARANTHA ™ | 59' | 302 | 220 | 24 | 215 |

FIG. 3A is a series of graphs depicted in three dimensions (in a rectangular mode for the "X" and "Y" axes) showing the relative attractiveness or repellency of GERANIOL COEUR™, ISOPROXEN™, hexyl cinnamic aldehyde, opoponax absolute, MARANTHA™, cis-3-hexenyl acetate, LYRAL®, GERALDEHYDE™, FLORALATE™ and air. The graph indicated by reference numeral 63 is for FLORALATE™. The graph indicated by reference numeral 65 is for ISOPROXEN™. The graph indicated by reference numeral 62 is for LYRAL®. The graph indicated by reference numeral 63 is for FLORALATE™. The graph indicated by reference numeral 64 is for GERALDEHYDE™. The graph indicated by reference numeral 61 is for hexyl cinnamic aldehyde. The graph indicated by reference numeral 66 is for opoponax absolute. The graph indicated by reference numeral 67 is for cis-3-hexenyl acetate. The graph indicated by reference numeral 68 is for GERANIOL COEUR™. The graph indicated by reference numeral 60 is for air. The test data is for mosquitoes, Aedes aegypti. The graphs are based on experiments run for a period of one hour with six intervals of ten minutes each. The results are tabulated in Table I (A) below.

FIG. 3B is a series of graphs depicted in three dimensions (in a rectangular mode for the "X" and "Y" axes) showing the relative attractiveness or repellency of GERANIOL COEUR , ISOPROXEN , hexyl cinnamic aldehyde, opoponax absolute, MARANTHA™, cis-3-hexenyl acetate, LYRAL®, GERALDEHYDE™, FLORALATE™ and air with reference to attractiveness or repellency for Aedes aegypti. The graphs are based on experiments run for a period of six hours with six intervals of one hour each. The graph indicated by reference numeral 63' is for FLORALATE™. The graph indicated by reference numeral 65' is for ISOPROXEN™. The graph indicated by reference numeral 62' is for LYRAL®. The graph indicated by reference numeral 63' is for FLORALATE™. The graph indicated by reference numeral 64' is for GERALDEHYDE™. The graph indicated by reference numeral 61' is for hexyl cinnamic aldehyde The graph indicated by reference numeral 66' is for opoponax absolute. The graph indicated by reference numeral 67' is for cis-3-hexenyl acetate. The graph indicated by reference numeral 68' is for GERANIOL COEUR™. The graph indicated by reference numeral 69' is for MARANTHA™. The results are tabulated in Table I(B) below.

TABLE I(A)

| Composition Tested | Graph No. | Insects Collected Per Interval of Ten Minutes Each | | | | | |
|---|---|---|---|---|---|---|---|
| ISOPROXEN ™ | 65 | 1 | 1 | 1 | 0 | 100 | 0 |
| hexyl cinnamic aldehyde | 61 | 60 | 193 | 372 | 24 | 48 | 17 |
| Opoponax absolute | 66 | 0 | 0 | 0 | 82 | 15 | 0 |
| MARANTHA ™ | 69 | 27 | 181 | 0 | 107 | 122 | 104 |
| Cis-3-hexenyl acetate | 67 | 1 | 123 | 126 | 85 | 146 | 321 |
| LYRAL ® | 62 | 2 | 10 | 2 | 3 | 12 | 5 |
| GERALDEHYDE ™ | 64 | 0 | 1 | 1 | 1 | 5 | 0 |
| FLORALATE ™ | 63 | 1 | 0 | 0 | 0 | 0 | 0 |
| Air | 60 | 86 | 427 | 362 | 183 | 144 | 177 |
| GERANIOL COEUR ™ natural | 68 | 1 | 0 | 0 | 0 | 0 | 9 |

TABLE I(B)

| Composition Tested | Graph No. | Insects Collected Per Interval of One Hour Each | | | | | |
|---|---|---|---|---|---|---|---|
| ISOPROXEN ™ | 65' | 0 | 2 | 26 | 80 | 298 | 209 |
| hexyl cinnamic aldehyde | 61' | 17 | 108 | 53 | 99 | 58 | 101 |
| Opoponax absolute | 66' | 0 | 3 | 34 | 17 | 0 | 0 |
| MARANTHA ™ | 69' | 104 | 30 | 52 | 121 | 39 | 60 |
| Cis-3-hexenyl acetate | 67' | 321 | 194 | 122 | 65 | 445 | 119 |
| LYRAL ® | 62' | 5 | 187 | 22 | 38 | 5 | 15 |
| GERALDE-HYDE ™ | 64' | 0 | 0 | 3 | 2 | 1 | 2 |
| FLORALATE ™ | 63' | 0 | 0 | 0 | 1 | 0 | 0 |

TABLE I(B)-continued

| Composition Tested | Graph No. | Insects Collected Per Interval of One Hour Each | | | | | |
|---|---|---|---|---|---|---|---|
| Air | 60' | 177 | 175 | 211 | 106 | 410 | 236 |
| GERANIOL COEUR ™ natural | 68' | 0 | 0 | 0 | 0 | 0 | 0 |

FIG. 4A is a bar graph showing mean bites per hour by Aedes aegypti on the "Y" axis (indicated by reference numeral 40) versus treatment substance (on the "X" axis indicated by reference numeral 41). The graph indicated by reference numeral 75 is for ISOPROXEN™. The graph indicated by reference numeral 71 is for hexyl cinnamic aldehyde. The graph indicated by reference numeral 76 is for opoponax absolute. The graph indicated by reference numeral 79 is for MARANTHA™. The graph indicated by reference numeral 77 is for cis-3-hexenyl acetate. The graph indicated by reference numeral 72 is for LYRAL®. The graph indicated by reference numeral 74 is for GERALDE-HYDE™. The graph indicated by reference numeral 73 is for FLORALATE™. The graph indicated by reference numeral 70 is for air. The graph indicated by reference numeral 78 is for GERANIOL COEUR™ natural. The graph set forth in FIG. 4B covers the same data as the graph indicated in FIG. 4A except that it is in three dimensions.

The data set forth in FIGS. 4A and 4B are obtained using the semiochemical field trap of FIG. 21, having six ports with three infrared light-emitting diodes.

FIG. 5 is a three-dimensional graph showing bite seconds on the "Y" axis by Aedes aegypti (indicated by reference numeral 42), treatment substance on the "X" axis and time on the "Z" axis. The graph indicated by reference numeral 87 is for thyme oil red, the composition of which is set forth in the GLC profile of FIG. 7A and FIG. 7B. The graph indicated by reference numeral 84 is for GERALDE-HYDE™. The graph indicated by reference numeral 86 is for eugenol. The graph indicated by reference numeral 85 is for sage oil. The graph indicated by reference numeral 88a is for GERANIOL COEUR™ synthetic, produced according to Example II, infra. The graph indicated by reference numeral 83 is for commercially available floral cosmetic fragrance "Floral No. 42A". The graph indicated by reference numeral 88b is also for GERANIOL COEUR™ synthetic, prepared according to Example II. The graph indicated by reference numeral 82 is for commercially available skin conditioner "C-1F" containing bay leaf oil. The graph indicated by reference numeral 81 is for glycerine (a standard attractant). The graph indicated by reference numeral 80 is for air.

FIG. 6 is based on the same data as is FIG. 5. FIG. 6 is a pie chart showing percentage attractancy for Aedes aegypti by the various substances as set forth in FIG. 5. The portion of the pie chart indicated by reference numeral 87' is for thyme oil red (1%). The portion of the pie chart indicated by reference numeral 84' is for GERALDEHYDE™ (4%). The portion of the pie chart indicated by reference numeral 86' is for eugenol (3%). The portion of the pie chart indicated by reference numeral 85' is for sage oil (4%). The portion of the pie chart indicated by reference numeral 88a' is for GERANIOL COEUR™ synthetic, prepared according to Example II (2%). The portion of the pie chart indicated by reference numeral 83' is for commercially available floral cosmetic fragrance "Floral 42A" (1%). The portion of the pie chart indicated by reference numeral 88b' is for GERANIOL COEUR™ synthetic, prepared according to Example II (4%). The portion of the pie chart indicated by reference numeral 82' is for commercially available skin conditioner "C-1F" containing bay leaf oil (43%). The portion of the pie chart indicated by reference numeral 81' is for glycerine (33%). The portion of the pie chart indicated by reference numeral 80' is for air (5%).

FIG. 7A is a GLC profile for thyme oil red contained in the results shown in FIGS. 5 and 6 (conditions: dual fused silica system: 50 meter Carbowax 20M column programmed from 70°–220° C. at 4° C. per minute). The peak indicated by reference numeral 90 is for α-pinene. The peak indicated by reference numeral 91 is for camphene. The peak indicated by reference numeral 92 is for myrcene. The peak indicated by reference numeral 93 is for α-terpinene. The peak indicated by reference numeral 94 is for γ-terpinene. The peak indicated by reference numeral 95 is for camphor. The peak indicated by reference numeral 96 is for linalool. The peak indicated by reference numeral 97 is for 4-terpineol. The peak indicated by reference numeral 98 is for borneol. The peak indicated by reference numeral 902 is for β-caryophyllene. The peak indicated b reference numeral 902' is for α-terpineol. The peak indicated by reference numeral 901 is for thymol. The peak indicated by reference numeral 99 is for carvacrol.

FIG. 7B is a GLC profile also for thyme oil red used in the results shown in FIGS. 5 and 6, supra (conditions: dual fused silica system: 50 meter OV-1 column programmed from 70°–220° C. at 4° C. per minute).

The peak indicated by reference numeral 90' is for α-pinene. The peak indicated by reference numeral 91' is for camphene. The peak indicated by reference numeral 92' is for myrcene. The peak indicated by reference numeral 93' is for α-terpinene. The peak indicated by reference numeral 94' is for γ-terpinene. The peak indicated by reference numeral 95' is for camphor. The peak indicated by reference numeral 96' is for linalool. The peak indicated by reference numeral 97' is for 4-terpineol. The peak indicated by reference numeral 98' is for borneol. The peak indicated by reference numeral 99' is for carvacrol. The peak indicated by reference numeral 901' is for thymol. The peak indicated by reference numeral 902' is for α-terpineol. The peak indicated by reference numeral 902" is for β-caryophyllene. The peak indicated by reference numeral 905' is for thymol methyl ether.

In referring to the extruder of FIG. 9, polymer 12 and 13 is admixed in vessel 14 and added at barrel segment S-1 of barrel 16 to the extruder which is powered by motor 15 held in place by bracket 23A. Simultaneously, into barrel segment S-6 (one of segments 18a, 18b, 18c or 18d) is added the insect repellent which is one or more of the unsaturated aldehyde or alkanol derivative-containing compositions of our invention previously held in container 17. The repellent/ perfumant mixture is pumped through pump 23 into barrel segment 18c/S-6. Simultaneously, foaming agent is added from vessel 19 into barrel segment S-8 from barrel segment S-10, a foamed tow containing polymer having imbedded therein insect repellent/perfume is passed through cooling bath 20 and the cooled tow 22 is then passed into mascerating machine 21 wherein the tow is chopped into particles and held in container 21a for future use, e.g., for use in conjunction with the manufacture of the insect repellent soap or detergent bars described in detail, infra.

Referring to FIGS. 11–20, inclusive, a preferred embodiment of our invention comprises an ellipsoidally-shaped detergent tablet 830. A preferred embodiment of our invention comprises an ellipsoidally-shaped detergent tablet 830 containing a solid plastic core 832 which can be fabricated from, for example, polyethylene, polypropylene, nylon, a biodegradable polymer such as poly (epsilon caprolactone) or any polymer capable of having therein microvoids from which an insect repelling/perfuming substance, e.g., at least one of the appropriate unsaturated aldehyde or alkanol derivative-containing compositions of our invention will be controllably transported from the plastic core into and through the soap cake over a reasonable period of time during the use of the soap cake. Such polymers can be microporous polymers, such as those described in U.S. Pat. No. 4,247,498 issued on Jan. 27, 1981 the specification for which is incorporated herein by reference. Surrounding the central plastic core containing insect repellent 832, is detergent 830' which is in the solid phase at ambient conditions, e.g., room temperature and atmospheric pressure. Examples of workable detergents 830' are "elastic" detergents such as those described in U.S. Pat. No. 4 181,632 issued on Jan. 1, 1980 the disclosure of which is incorporated herein by reference, or "transparent" soaps such as those set forth in U.S. Pat. No. 4,165,293 issued on Aug. 21, 1979 the disclosure of which is incorporated herein by reference. Other examples of the detergent 830' useful in our invention are those set forth as "variegated soaps" in Canadian Patent No. 1,101,165 issued on May 19, 1981.

On use of the soap tablet 830 or detergent bar, the insect repellent agent originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelepiped tablet as shown in FIGS. 15, 16 and 17 containing solid plastic core 839. The insect repellent located in solid plastic core 839 on use of the detergent bar passes through at steady state, surface 837 of FIG. 16, detergent 838 and finally surface 839 at, for example, locations 840, 841, 842 and 843. The environment surrounding the detergent bar on use thereof is then treated with the insect repellent at 843, 844 and 845, for example. Optionally, aromatizing agent can also be contained in the detergent bar (if desired) and so the environment surrounding the detergent bar on use thereof would also be aesthetically aromatized at 843, 844 and 845, for example, if the appropriate unsaturated aldehyde or alkanol derivative-containing composition of our invention is insufficient for such aromatization. In certain instances, such appropriate unsaturated aldehyde or alkanol derivative-containing compositions are indeed sufficient for such aromatization.

As is shown in FIGS. 18, 19 and 20, the plastic core of the detergent tablet 830 may have a single finite void at its center 851 (of FIGS. 19 and 20) in which the insect repellent agent and, optionally, any additional aromatizing agents are contained. The plastic core is a shell 848 having outer surface 852 (shown in FIGS. 19 and 20). The insect repellent agent (and, optionally, any additional aromatizing agent) contained in the void in the plastic core permeates through shell 848, past surface 852 at a steady state, through the detergent 847 and to the environment at, for example, 856, 857, 858 and 859.

In addition to the insect repellent contained in the core, e.g., core 839 or core void, the core can also contain other materials for therapeutic use, for example, bacteriastats, deodorizing agents and the like which are compatible with appropriate unsaturated aldehyde or alkanol derivative-containing compositions of our invention. In the alternative, the plastic core of the detergent tablet of FIGS. 18, 19 and 20 may have an empty single finite void at its center 851 with the insect repellent contained in the shell 848.

At the end of the use of the detergent tablet, the hollow core or the solid core can be used as an insect imparting and aroma imparting or air freshener household article. In addition, depending on the ratio of the volume of the void 851 to the solid part of the detergent tablet of FIGS. 18, 19 and 20, the detergent tablet of FIGS. 18, 19 and 20 can be so fabricated that it will float on the surface of the liquid in which it is being used and this physical attribute has certain obvious advantages.

FIG. 22 is the GLC profile for GERANIOL COEUR™ natural produced according to Example I, infra. The peak indicated by reference numeral 1081 is the peak for geraniol having the structure:

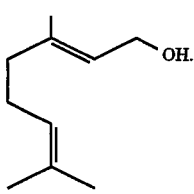

The peak indicated by reference numeral 1082 is for nerol having the structure:

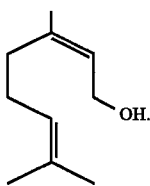

The peak indicated by reference numeral 1083 is for α-citronellol having the structure:

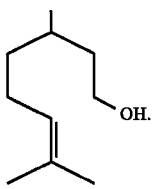

The peaks indicated by reference numerals 1084 and 1085 are for β-citronellol having the structure:

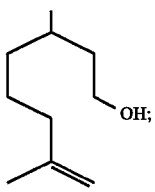

and in addition, 3,7-dimethyl octanol-1 having the structure:

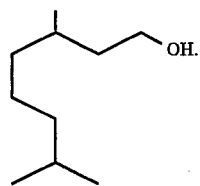

Other materials also are contained in GERANIOL COEUR™ but are of unknown chemical constituency and those are the peaks indicated by reference numerals 1086, 1087, 1088 and 1089. Included in the peaks indicated by reference numeral 1087 is the compound β-elemene having the structure:

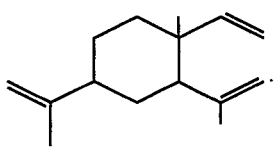

FIG. 23 is the GLC profile for GEBANIOL COEUR™ synthetic (produced according to Example II, infra). The peak indicated by reference numeral 1091 is the peak for geraniol having the structure:

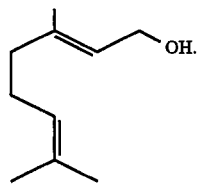

The peak indicated by reference numeral 1092 is the peak for nerol having the structure:

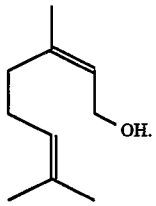

The peak indicated by reference numeral 1093 is the peak for α-citronellol having the structure:

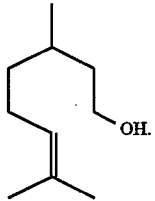

The peak indicated by reference numeral 1094 is the peak for 3,7-dimethyl octanol-1 having the structure:

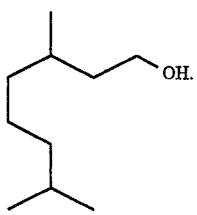

The peaks indicated by reference numerals 1095, 1096, 1097 and 1098 are for additional materials contained in GERANIOL COEUR™ synthetic which are of unknown constituency.

The following examples are illustrative and the instant Patent Application is intended to be restricted only to the scope of the claims and not to the examples.

EXAMPLE I

PREPARATION OF GERANIOL COEUR™ NATURAL

Palmarosa oil is steam distilled from wild growing, fresh grass of the plant *Cymbopogon Martini*, varietas motia grown in Northeast Katmandu, Nepal. One part of Palmarosa oil is admixed with 4 parts of a 50:50 mixture of sodium hydroxide and methyl alcohol. The resulting mixture is heated at reflux for a period of one hour. 3.5 Parts of anhydrous methanol is then added to the resulting mixture. The resulting mixture is then steam distilled at 100 mm/Hg pressure. GERANIOL COEUR™ natural distills as the middle cut having a refractive index of 1.469–1.475 and a specific gravity at 20°/4° C. of 0.869–0.877. FIG. 22 is the GLC profile for the GERANIOL COEUR™ natural.

EXAMPLE II

PREPARATION OF GERANIOL COEUR™ SYNTHETIC

100 Grams of citronella oil (Java) is admixed with 50 ml of heptane. The resulting mixture is heated on a boiling water bath at 100° C. in a 1 liter flask for a period of one hour. At the end of the one hour period, 8 grams of sodium metal are slowly added to the resulting mixture. The addition of sodium metal takes place over a period of 0.5 hours. The resulting mixture is then filtered. Unreacted sodium is removed and the filtered complex-containing oil is maintained at a temperature of 5° C. for a period of 10 hours. The resulting crystalline product is then filtered and weighs 32 grams. The resulting product is then hydrodistilled in a 2 liter flask with 1.5 liters of water. The hydrodistillate fractions of 100 ml are collected. After separating the aqueous phase from the organic phase, the resulting fractions are analyzed via thin layer chromatography. The fractions are as follows:

| FRACTION NO. | WEIGHT (Grams) | REFRACTIVE INDEX | DENSITY |
|---|---|---|---|
| 1 | 4.5 | 1.456 | 0.8535 |
| 2 | 7.1 | 1.468 | 0.868 |
| 3 | 6.9 | 1.469 | 0.873 |
| 4 | 6.5 | 1.473 | 0.8755 |

Fractions 2, 3 and 4 are then combined to form GERANIOL COEUR™ synthetic. The GLC profile for the GERANIOL COEUR™ synthetic is set forth in FIG. 23.

EXAMPLE III

A transparent candle base mixture is produced by intimately admixing the following ingredients:

| Ingredients | Parts by Weight |
|---|---|
| VERSAMID® 1635 | 34.0 |
| Barlol 12C2 | 51.0 |
| Butyl stearate | 3.5 |
| NEVEX® 100 | 5.0 |
| SPAN® | 1.5 |
| Isopropyl isostearate | 4.0 |
| Isopropyl myristate | 4.0 |

The foregoing mixture is placed in an autoclave and intimately admixed with 22% by weight of the entire mixture of a perfuming-insect repellent composition containing the following ingredients:

| Ingredients | Parts by Weight |
|---|---|
| LYRAL®, a 50:50 mixture of compounds having the structures: | 50 |
| GERALDEHYDE™ having the structure: | 50 |

The autoclave is sealed and heated to 180° C. under 25 atmospheres pressure and maintained with vigorous shaking for a period of 5 hours. At the end of the 5 hour period, the autoclave is depressurized (being under a nitrogen pressure atmosphere) and the autoclave is opened and the contents are then poured into cylindrical candle molds 4" in height and 2" in diameter containing 0.125" wicks. The resulting candles have efficacious *Aedes aegypti*, *Aedes albopictus* and *Musca domestica L.* repellencies and have aesthetically pleasing aromas on use.

The candles are effective in preventing houseflies and the mosquito species *Aedes aegypti* and *Aedes albopictus* from entering a room in which four candles have been burning for 15 minutes, the said room having dimensions of 6'×15'×15' and having a 2'×2' open portal adjacent to a housefly and mosquito-infested region in the month of August 1995 in the temperate zone of Highlands, N.J. adjacent Raritan Bay.

EXAMPLE IV

A study was conducted to evaluate the efficacy of candles which ate designate as A, B and C in repelling the mosquito species, *Aedes aegypti*.

Candle A contained 95% paraffin wax and 5% of GERANIOL COEUR™ natural prepared according to Example I and having the GLC profile of FIG. 22.

Candle B contained 90% paraffin wax and 10% citronella oil.

Candle C contained only paraffin wax.

The candles are allowed to burn for 20 minutes and the number of the mosquitoes (*Aedes aegypti*) repelled is recorded for the next 60 minutes with the following equipment and procedure:

Materials

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4 cm hole located in the center of each Masonite plate provided an escape for the test insects. A barrier was used to close the hole.

Attractant

A caged grey mouse was used as an attractant and was placed inside the chamber in the larger section of the repellency cage.

Test Insects

*Aedes aegypti* mosquitoes

Procedure

For each replicate, 75 to 100 *Aedes aegypti* mosquitoes were removed from the rearing cage by means of a vacuum aspirator and transferred by carbon dioxide anesthesia to the inner cage containing the grey mouse. The assembled cage was placed in one of the upper ventilation ports of the chamber. For each experimental situation, the test insects were transferred to a clean cage containing the mouse. A candle containing the insect repellent substance to be tested was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of *Aedes aegypti* mosquitoes repelled were those escaping to the outside cage. For the control, counts were made in a similar manner, but no candle was burned.

The same three candles were used for all four replicates. Between replicates, the chamber was exhausted, the Kraft paper flooring for the chamber was replaced and the two screened repellency cages were submerged in hot detergent water, rinsed and dried.

Results

The overall average percent of *Aedes aegypti* mosquitoes repelled for each candle for 60 minutes was as follows:

Candle A—97%;
Candle B—48%; and
Candle C—14%.

What is claimed is:

1. A method of repelling the insect species: *Aedes aegypti* for a finite period of time from a three-dimensional space inhabited by said *Aedes aegypti* consisting essentially of the step of exposing said three-dimensional space to an effective Aedes aegypti-repelling concentration and quantity of at least one substance selected from the group consisting of:

(i) a mixture of compounds having the structures:

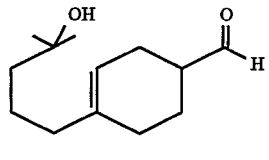

and

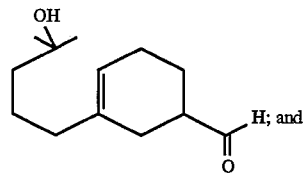

and (ii) a compound having the structure:

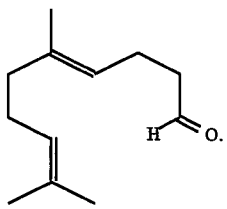

2. The method of claim 1 wherein the insect repelling substance is a mixture of compounds having the structures:

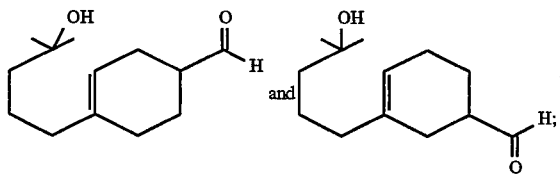

3. The method of claim 1 wherein the insect repelling substance is a compound having the structure:

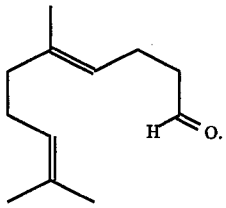

4. The method of claim 1 wherein the insect repelling substance is contained in a polymer matrix.

5. The method of claim 4 wherein the polymer matrix consists of a biodegradable polymer.

6. The method of claim 5 wherein the biodegradable polymer is a polycaprolactone polymer or a polyurethane polymer.

7. The method of claim 1 wherein the insect repellent substance is initially admixed with a soap base; the resulting mixture is formulated into a soap article; and the resulting soap article is applied in a washing procedure on a person in need of *Aedes aegypti* repellence.

8. The method of claim 7 wherein the insect repellent substance is contained in a polymer matrix, and the polymer matrix containing said substance is formed into a core and surrounded with a soap base; and the resulting article is applied in a washing procedure to a person in need of *Aedes aegypti* repellence.

* * * * *